United States Patent
Childs et al.

(10) Patent No.: US 12,414,811 B2
(45) Date of Patent: Sep. 16, 2025

(54) DEVICES AND METHODS FOR LEAFLET CUTTING

(71) Applicant: Evalve, Inc., Santa Clara, CA (US)

(72) Inventors: Richard Thomas Childs, San Francisco, CA (US); Scott C. Mosher, San Francisco, CA (US); Lauren Troxler Harvey, Austin, TX (US); Koji J. Kizuka, Redwood City, CA (US); Ajitkumar B. Nair, Pleasanton, CA (US); Laura M. Kalvass, Mountain View, CA (US)

(73) Assignee: Evalve, Inc., Santa Clara, CA (US)

( * ) Notice: Subject to any disclaimer, the term of this patent is extended or adjusted under 35 U.S.C. 154(b) by 22 days.

(21) Appl. No.: 17/306,398

(22) Filed: May 3, 2021

(65) Prior Publication Data
US 2021/0346081 A1    Nov. 11, 2021

Related U.S. Application Data

(60) Provisional application No. 63/020,669, filed on May 6, 2020.

(51) Int. Cl.
*A61B 18/00* (2006.01)
*A61B 18/14* (2006.01)

(52) U.S. Cl.
CPC ...... *A61B 18/1442* (2013.01); *A61B 18/1492* (2013.01); *A61B 2018/00369* (2013.01);
(Continued)

(58) Field of Classification Search
CPC ............ A61B 18/1442; A61B 18/1492; A61B 2018/00369; A61B 2018/1452; A61B 2017/00783
See application file for complete search history.

(56) References Cited

U.S. PATENT DOCUMENTS

| | | | |
|---|---|---|---|
| 1,996,261 | A | 4/1935 | Storz |
| 2,097,018 | A | 10/1937 | Chamberlin |

(Continued)

FOREIGN PATENT DOCUMENTS

| | | |
|---|---|---|
| CN | 1469724 A | 1/2004 |
| CN | 102770080 A | 11/2012 |

(Continued)

OTHER PUBLICATIONS

Kruger et al., "P73—Edge to Edge Technique in Complex Mitral Valve Repair," Thorac Cardiovasc Surg., 48(Suppl. 1):106 (2000).
(Continued)

*Primary Examiner* — Joseph A Stoklosa
*Assistant Examiner* — Annie L Shoulders
(74) *Attorney, Agent, or Firm* — Workman Nydegger

(57) ABSTRACT

A system for cutting leaflet tissue at a cardiac valve may comprise a guide catheter having a proximal end and a distal end, wherein the distal end of the guide catheter is steerable to a position above a cardiac valve. The system may also include a handle coupled to the proximal end of the guide catheter, the handle comprising at least one control configured to steer the guide catheter to the position above the cardiac valve. Finally, the system may comprise a cutting mechanism routable through the guide catheter and able to be positioned at the distal end of the guide catheter, the cutting mechanism configured to cut a portion of leaflet tissue of the cardiac valve.

21 Claims, 16 Drawing Sheets

(52) U.S. Cl.
CPC .............. *A61B 2018/0072* (2013.01); *A61B 2018/1452* (2013.01)

(56) References Cited

U.S. PATENT DOCUMENTS

| | | | |
|---|---|---|---|
| 2,108,206 A | 2/1938 | Mecker |
| 3,296,668 A | 1/1967 | Aiken |
| 3,378,010 A | 4/1968 | Codling et al. |
| 3,470,875 A | 10/1969 | Johnson |
| 3,557,780 A | 1/1971 | Sato |
| 3,671,979 A | 6/1972 | Moulopoulos |
| 3,675,639 A | 7/1972 | Cimber |
| 3,776,237 A | 12/1973 | Hill et al. |
| 3,874,338 A | 4/1975 | Happel |
| 3,874,388 A | 4/1975 | King et al. |
| 4,007,743 A | 2/1977 | Blake |
| 4,056,854 A | 11/1977 | Boretos et al. |
| 4,064,881 A | 12/1977 | Meredith |
| 4,091,815 A | 5/1978 | Larsen |
| 4,112,951 A | 9/1978 | Hulka et al. |
| 4,235,238 A | 11/1980 | Ogiu et al. |
| 4,297,749 A | 11/1981 | Davis et al. |
| 4,312,337 A | 1/1982 | Donohue |
| 4,425,908 A | 1/1984 | Simon |
| 4,458,682 A | 7/1984 | Cerwin |
| 4,484,579 A | 11/1984 | Meno et al. |
| 4,487,205 A | 12/1984 | Di et al. |
| 4,498,476 A | 2/1985 | Cerwin et al. |
| 4,510,934 A | 4/1985 | Batra |
| 4,531,522 A | 7/1985 | Bedi et al. |
| 4,578,061 A | 3/1986 | Lemelson |
| 4,641,366 A | 2/1987 | Yokoyama et al. |
| 4,686,965 A | 8/1987 | Bonnet et al. |
| 4,777,951 A | 10/1988 | Cribier et al. |
| 4,809,695 A | 3/1989 | Gwathmey et al. |
| 4,872,455 A | 10/1989 | Pinchuk et al. |
| 4,878,495 A | 11/1989 | Grayzel |
| 4,917,089 A | 4/1990 | Sideris |
| 4,944,295 A | 7/1990 | Gwathmey et al. |
| 4,969,890 A | 11/1990 | Sugita et al. |
| 4,994,077 A | 2/1991 | Dobben |
| 5,015,249 A | 5/1991 | Nakao et al. |
| 5,019,096 A | 5/1991 | Fox et al. |
| 5,042,707 A | 8/1991 | Taheri |
| 5,047,041 A | 9/1991 | Samuels |
| 5,049,153 A | 9/1991 | Nakao et al. |
| 5,053,043 A | 10/1991 | Gottesman et al. |
| 5,061,277 A | 10/1991 | Carpentier et al. |
| 5,069,679 A | 12/1991 | Taheri |
| 5,071,428 A | 12/1991 | Chin et al. |
| 5,078,722 A | 1/1992 | Stevens |
| 5,078,723 A | 1/1992 | Dance et al. |
| 5,108,368 A | 4/1992 | Hammerslag et al. |
| 5,125,758 A | 6/1992 | Dewan |
| 5,171,252 A | 12/1992 | Friedland |
| 5,171,259 A | 12/1992 | Inoue |
| 5,190,554 A | 3/1993 | Coddington et al. |
| 5,195,968 A | 3/1993 | Lundquist et al. |
| 5,209,756 A | 5/1993 | Seedhom et al. |
| 5,217,460 A | 6/1993 | Knoepfler |
| 5,226,429 A | 7/1993 | Kuzmak |
| 5,226,911 A | 7/1993 | Chee et al. |
| 5,234,437 A | 8/1993 | Sepetka |
| 5,242,456 A | 9/1993 | Nash et al. |
| 5,250,071 A | 10/1993 | Palermo |
| 5,251,611 A | 10/1993 | Zehel et al. |
| 5,254,130 A | 10/1993 | Poncet et al. |
| 5,261,916 A | 11/1993 | Engelson |
| 5,271,381 A | 12/1993 | Ailinger et al. |
| 5,275,578 A | 1/1994 | Adams |
| 5,282,845 A | 2/1994 | Bush et al. |
| 5,304,131 A | 4/1994 | Paskar |
| 5,306,283 A | 4/1994 | Conners |
| 5,306,286 A | 4/1994 | Stack et al. |
| 5,312,415 A | 5/1994 | Palermo |
| 5,314,424 A | 5/1994 | Nicholas |
| 5,318,525 A | 6/1994 | West et al. |
| 5,320,632 A | 6/1994 | Heidmueller |
| 5,325,845 A | 7/1994 | Adair |
| 5,330,442 A | 7/1994 | Green et al. |
| 5,332,402 A | 7/1994 | Teitelbaum |
| 5,336,227 A | 8/1994 | Nakao et al. |
| 5,342,393 A | 8/1994 | Stack |
| 5,350,397 A | 9/1994 | Palermo et al. |
| 5,350,399 A | 9/1994 | Erlebacher et al. |
| 5,359,994 A | 11/1994 | Krauter et al. |
| 5,368,564 A | 11/1994 | Savage |
| 5,368,601 A | 11/1994 | Sauer et al. |
| 5,373,854 A | 12/1994 | Kolozsi |
| 5,383,886 A | 1/1995 | Kensey et al. |
| 5,387,219 A | 2/1995 | Rappe |
| 5,391,182 A | 2/1995 | Chin |
| 5,395,030 A | 3/1995 | Kuramoto et al. |
| 5,403,312 A | 4/1995 | Yates et al. |
| 5,403,326 A | 4/1995 | Harrison et al. |
| 5,411,552 A | 5/1995 | Andersen et al. |
| 5,417,684 A | 5/1995 | Jackson et al. |
| 5,417,699 A | 5/1995 | Klein et al. |
| 5,417,700 A | 5/1995 | Egan |
| 5,423,830 A | 6/1995 | Schneebaum et al. |
| 5,423,857 A | 6/1995 | Rosenman et al. |
| 5,423,858 A | 6/1995 | Bolanos et al. |
| 5,423,882 A | 6/1995 | Jackman et al. |
| 5,431,666 A | 7/1995 | Sauer et al. |
| 5,437,551 A | 8/1995 | Chalifoux |
| 5,437,681 A | 8/1995 | Meade et al. |
| 5,447,966 A | 9/1995 | Hermes et al. |
| 5,450,860 A | 9/1995 | O'Connor |
| 5,456,400 A | 10/1995 | Shichman et al. |
| 5,456,684 A | 10/1995 | Schmidt et al. |
| 5,462,527 A | 10/1995 | Stevens-Wright et al. |
| 5,472,044 A | 12/1995 | Hall et al. |
| 5,472,423 A | 12/1995 | Gronauer |
| 5,476,470 A | 12/1995 | Fitzgibbons, Jr. |
| 5,477,856 A | 12/1995 | Lundquist |
| 5,478,309 A | 12/1995 | Sweezer et al. |
| 5,478,353 A | 12/1995 | Yoon |
| 5,487,746 A | 1/1996 | Yu et al. |
| 5,496,332 A | 3/1996 | Sierra et al. |
| 5,507,725 A | 4/1996 | Savage et al. |
| 5,507,755 A | 4/1996 | Gresl et al. |
| 5,507,757 A | 4/1996 | Sauer et al. |
| 5,520,701 A | 5/1996 | Lerch |
| 5,522,873 A | 6/1996 | Jackman et al. |
| 5,527,313 A | 6/1996 | Scott et al. |
| 5,527,321 A | 6/1996 | Hinchliffe |
| 5,527,322 A | 6/1996 | Klein et al. |
| 5,536,251 A | 7/1996 | Evard et al. |
| 5,540,705 A | 7/1996 | Meade et al. |
| 5,542,949 A | 8/1996 | Yoon |
| 5,554,185 A | 9/1996 | Block et al. |
| 5,562,678 A | 10/1996 | Booker |
| 5,569,274 A | 10/1996 | Rapacki et al. |
| 5,571,085 A | 11/1996 | Accisano, III |
| 5,571,137 A | 11/1996 | Marlow et al. |
| 5,571,215 A | 11/1996 | Sterman et al. |
| 5,575,802 A | 11/1996 | McQuilkin et al. |
| 5,582,611 A | 12/1996 | Tsuruta et al. |
| 5,584,803 A * | 12/1996 | Stevens ............ A61M 25/0147 604/6.16 |
| 5,593,424 A | 1/1997 | Northrup, III |
| 5,593,435 A | 1/1997 | Carpentier et al. |
| 5,609,598 A | 3/1997 | Laufer et al. |
| 5,617,854 A | 4/1997 | Munsif |
| 5,618,306 A | 4/1997 | Roth et al. |
| 5,620,452 A | 4/1997 | Yoon |
| 5,620,461 A | 4/1997 | Muijs et al. |
| 5,626,588 A | 5/1997 | Sauer et al. |
| 5,634,932 A | 6/1997 | Schmidt |
| 5,636,634 A | 6/1997 | Kordis et al. |
| 5,639,277 A | 6/1997 | Mariant et al. |
| 5,640,955 A | 6/1997 | Ockuly et al. |
| 5,649,937 A | 7/1997 | Bito et al. |
| 5,662,681 A | 9/1997 | Nash et al. |

(56) References Cited

U.S. PATENT DOCUMENTS

| | | |
|---|---|---|
| 5,669,917 A | 9/1997 | Sauer et al. |
| 5,669,919 A | 9/1997 | Sanders et al. |
| 5,690,671 A | 11/1997 | McGurk et al. |
| 5,695,504 A | 12/1997 | Gifford et al. |
| 5,695,505 A | 12/1997 | Yoon |
| 5,702,825 A | 12/1997 | Keita et al. |
| 5,706,824 A | 1/1998 | Whittier |
| 5,709,707 A | 1/1998 | Lock et al. |
| 5,713,910 A | 2/1998 | Gordon et al. |
| 5,713,911 A | 2/1998 | Racenet et al. |
| 5,715,817 A | 2/1998 | Stevens-Wright et al. |
| 5,716,367 A | 2/1998 | Koike et al. |
| 5,718,725 A | 2/1998 | Sterman et al. |
| 5,719,725 A | 2/1998 | Nakao |
| 5,722,421 A | 3/1998 | Francese et al. |
| 5,725,542 A | 3/1998 | Yoon |
| 5,725,556 A | 3/1998 | Moser et al. |
| 5,738,649 A | 4/1998 | Macoviak |
| 5,741,271 A | 4/1998 | Nakao et al. |
| 5,741,280 A | 4/1998 | Fleenor |
| 5,746,747 A | 5/1998 | McKeating |
| 5,749,828 A | 5/1998 | Yeung |
| 5,759,193 A | 6/1998 | Burbank et al. |
| 5,769,812 A | 6/1998 | Stevens et al. |
| 5,769,863 A | 6/1998 | Garrison |
| 5,772,578 A | 6/1998 | Heimberger et al. |
| 5,782,845 A | 7/1998 | Shewchuk |
| 5,797,927 A | 8/1998 | Yoon |
| 5,797,960 A | 8/1998 | Stevens et al. |
| 5,810,847 A | 9/1998 | Laufer et al. |
| 5,810,849 A | 9/1998 | Kontos |
| 5,810,853 A | 9/1998 | Yoon |
| 5,810,876 A | 9/1998 | Kelleher |
| 5,814,029 A | 9/1998 | Hassett |
| 5,820,591 A | 10/1998 | Thompson et al. |
| 5,820,592 A | 10/1998 | Hammerslag |
| 5,820,630 A | 10/1998 | Lind |
| 5,820,631 A | 10/1998 | Nobles |
| 5,823,955 A | 10/1998 | Kuck et al. |
| 5,823,956 A | 10/1998 | Roth et al. |
| 5,824,065 A | 10/1998 | Gross |
| 5,827,237 A | 10/1998 | Macoviak et al. |
| 5,829,447 A | 11/1998 | Stevens et al. |
| 5,833,671 A | 11/1998 | Macoviak et al. |
| 5,836,955 A | 11/1998 | Buelna et al. |
| 5,840,081 A | 11/1998 | Andersen et al. |
| 5,843,031 A | 12/1998 | Hermann et al. |
| 5,843,103 A | 12/1998 | Wulfman |
| 5,849,019 A | 12/1998 | Yoon |
| 5,853,422 A | 12/1998 | Huebsch et al. |
| 5,855,271 A | 1/1999 | Eubanks et al. |
| 5,855,590 A | 1/1999 | Malecki et al. |
| 5,855,614 A | 1/1999 | Stevens et al. |
| 5,860,990 A | 1/1999 | Nobles et al. |
| 5,861,003 A | 1/1999 | Latson et al. |
| 5,868,733 A | 2/1999 | Ockuly et al. |
| 5,876,399 A | 3/1999 | Chia et al. |
| 5,879,307 A | 3/1999 | Chio et al. |
| 5,885,271 A | 3/1999 | Hamilton et al. |
| 5,891,160 A | 4/1999 | Williamson et al. |
| 5,895,404 A | 4/1999 | Ruiz |
| 5,895,417 A | 4/1999 | Pomeranz et al. |
| 5,906,620 A | 5/1999 | Nakao et al. |
| 5,908,420 A | 6/1999 | Parins et al. |
| 5,916,147 A | 6/1999 | Boury |
| 5,928,224 A | 7/1999 | Laufer |
| 5,944,733 A | 8/1999 | Engelson |
| 5,947,363 A | 9/1999 | Bolduc et al. |
| 5,954,732 A | 9/1999 | Hart et al. |
| 5,957,949 A | 9/1999 | Leonhardt et al. |
| 5,957,973 A | 9/1999 | Quiachon et al. |
| 5,972,020 A | 10/1999 | Carpentier et al. |
| 5,972,030 A | 10/1999 | Garrison et al. |
| 5,980,455 A | 11/1999 | Daniel et al. |
| 5,989,284 A | 11/1999 | Laufer |
| 5,997,547 A | 12/1999 | Nakao et al. |
| 6,007,546 A | 12/1999 | Snow et al. |
| 6,015,417 A | 1/2000 | Reynolds, Jr. |
| 6,019,722 A | 2/2000 | Spence et al. |
| 6,022,360 A | 2/2000 | Reimels et al. |
| 6,033,378 A | 3/2000 | Lundquist et al. |
| 6,033,419 A | 3/2000 | Hamblin et al. |
| 6,036,699 A | 3/2000 | Andreas et al. |
| 6,048,351 A | 4/2000 | Gordon et al. |
| 6,053,933 A | 4/2000 | Balazs et al. |
| 6,056,769 A | 5/2000 | Epstein et al. |
| 6,059,757 A | 5/2000 | Macoviak et al. |
| 6,060,628 A | 5/2000 | Aoyama et al. |
| 6,060,629 A | 5/2000 | Pham et al. |
| 6,063,106 A | 5/2000 | Gibson |
| 6,066,146 A | 5/2000 | Carroll et al. |
| 6,068,628 A | 5/2000 | Fanton et al. |
| 6,068,629 A | 5/2000 | Haissaguerre et al. |
| 6,077,214 A | 6/2000 | Mortier et al. |
| 6,086,600 A | 7/2000 | Kortenbach |
| 6,088,889 A | 7/2000 | Luther et al. |
| 6,090,118 A | 7/2000 | McGuckin, Jr. |
| 6,099,505 A | 8/2000 | Ryan et al. |
| 6,099,553 A | 8/2000 | Hart et al. |
| 6,110,145 A | 8/2000 | Macoviak |
| 6,117,144 A | 9/2000 | Nobles et al. |
| 6,117,159 A | 9/2000 | Huebsch et al. |
| 6,123,665 A | 9/2000 | Kawano |
| 6,123,699 A | 9/2000 | Webster, Jr. |
| 6,126,658 A | 10/2000 | Baker |
| 6,132,447 A | 10/2000 | Dorsey |
| 6,136,010 A | 10/2000 | Modesitt et al. |
| 6,139,508 A | 10/2000 | Simpson et al. |
| 6,143,024 A | 11/2000 | Campbell et al. |
| 6,159,240 A | 12/2000 | Sparer et al. |
| 6,162,233 A | 12/2000 | Williamson et al. |
| 6,165,164 A | 12/2000 | Hill et al. |
| 6,165,183 A | 12/2000 | Kuehn et al. |
| 6,165,204 A | 12/2000 | Levinson et al. |
| 6,168,614 B1 | 1/2001 | Andersen et al. |
| 6,171,320 B1 | 1/2001 | Monassevitch |
| 6,174,322 B1 | 1/2001 | Schneidt |
| 6,180,059 B1 | 1/2001 | Divino et al. |
| 6,182,664 B1 | 2/2001 | Cosgrove |
| 6,187,003 B1 | 2/2001 | Buysse et al. |
| 6,190,408 B1 | 2/2001 | Melvin |
| 6,197,043 B1 | 3/2001 | Davidson |
| 6,203,531 B1 | 3/2001 | Ockuly et al. |
| 6,203,553 B1 | 3/2001 | Robertson et al. |
| 6,206,893 B1 | 3/2001 | Klein et al. |
| 6,206,907 B1 | 3/2001 | Marino et al. |
| 6,210,419 B1 | 4/2001 | Mayenberger et al. |
| 6,210,432 B1 | 4/2001 | Solem et al. |
| 6,245,079 B1 | 6/2001 | Nobles et al. |
| 6,264,617 B1 | 7/2001 | Bales et al. |
| 6,267,746 B1 | 7/2001 | Bumbalough |
| 6,267,781 B1 | 7/2001 | Tu |
| 6,269,819 B1 | 8/2001 | Oz et al. |
| 6,277,555 B1 | 8/2001 | Duran et al. |
| 6,283,127 B1 | 9/2001 | Sterman et al. |
| 6,283,962 B1 | 9/2001 | Tu et al. |
| 6,299,637 B1 | 10/2001 | Shaolian et al. |
| 6,306,133 B1 | 10/2001 | Tu et al. |
| 6,312,447 B1 | 11/2001 | Grimes |
| 6,319,250 B1 | 11/2001 | Falwell et al. |
| 6,322,559 B1 | 11/2001 | Daulton et al. |
| 6,332,893 B1 | 12/2001 | Mortier et al. |
| 6,334,860 B1 | 1/2002 | Dorn |
| 6,352,708 B1 | 3/2002 | Duran et al. |
| 6,355,030 B1 | 3/2002 | Aldrich et al. |
| 6,358,277 B1 | 3/2002 | Duran |
| 6,368,326 B1 | 4/2002 | Dakin et al. |
| 6,387,104 B1 | 5/2002 | Pugsley et al. |
| 6,402,780 B2 | 6/2002 | Williamson et al. |
| 6,402,781 B1 | 6/2002 | Langberg et al. |
| 6,406,420 B1 | 6/2002 | McCarthy et al. |
| 6,419,640 B1 | 7/2002 | Taylor |
| 6,419,669 B1 | 7/2002 | Frazier et al. |
| 6,461,366 B1 | 10/2002 | Seguin |

(56) References Cited

U.S. PATENT DOCUMENTS

| | | |
|---|---|---|
| 6,464,707 B1 | 10/2002 | Bjerken |
| 6,482,224 B1 | 11/2002 | Michler et al. |
| 6,485,489 B2 | 11/2002 | Teirstein et al. |
| 6,494,881 B1 | 12/2002 | Bales et al. |
| 6,508,828 B1 | 1/2003 | Akerfeldt et al. |
| 6,517,550 B1 | 2/2003 | Konya et al. |
| 6,533,796 B1 | 3/2003 | Sauer et al. |
| 6,537,314 B2 | 3/2003 | Langberg et al. |
| 6,540,755 B2 | 4/2003 | Ockuly et al. |
| 6,551,331 B2 | 4/2003 | Nobles et al. |
| 6,562,037 B2 | 5/2003 | Paton et al. |
| 6,562,052 B2 | 5/2003 | Nobles et al. |
| 6,575,971 B2 | 6/2003 | Hauck et al. |
| 6,585,761 B2 | 7/2003 | Taheri |
| 6,599,311 B1 | 7/2003 | Biggs et al. |
| 6,616,684 B1 | 9/2003 | Vidlund et al. |
| 6,619,291 B2 | 9/2003 | Hlavka et al. |
| 6,626,899 B2 | 9/2003 | Houser et al. |
| 6,626,921 B2 | 9/2003 | Blatter et al. |
| 6,626,930 B1 | 9/2003 | Allen et al. |
| 6,629,534 B1 | 10/2003 | St et al. |
| 6,641,592 B1 | 11/2003 | Sauer et al. |
| 6,656,221 B2 | 12/2003 | Taylor et al. |
| 6,669,687 B1 | 12/2003 | Saadat |
| 6,685,648 B2 | 2/2004 | Flaherty et al. |
| 6,689,164 B1 | 2/2004 | Seguin |
| 6,695,866 B1 | 2/2004 | Kuehn et al. |
| 6,701,929 B2 | 3/2004 | Hussein |
| 6,702,825 B2 | 3/2004 | Frazier et al. |
| 6,702,826 B2 | 3/2004 | Liddicoat et al. |
| 6,709,382 B1 | 3/2004 | Horner |
| 6,709,456 B2 | 3/2004 | Langberg et al. |
| 6,718,985 B2 | 4/2004 | Hlavka et al. |
| 6,719,767 B1 | 4/2004 | Kimblad |
| 6,723,038 B1 | 4/2004 | Schroeder et al. |
| 6,726,716 B2 | 4/2004 | Marquez |
| 6,740,107 B2 | 5/2004 | Loeb et al. |
| 6,746,471 B2 | 6/2004 | Mortier et al. |
| 6,752,813 B2 | 6/2004 | Goldfarb et al. |
| 6,755,777 B2 | 6/2004 | Schweich et al. |
| 6,764,510 B2 | 7/2004 | Vidlund et al. |
| 6,767,349 B2 | 7/2004 | Ouchi |
| 6,770,083 B2 | 8/2004 | Seguin |
| 6,797,001 B2 | 9/2004 | Mathis et al. |
| 6,797,002 B2 | 9/2004 | Spence et al. |
| 6,860,179 B2 | 3/2005 | Hopper et al. |
| 6,875,224 B2 | 4/2005 | Grimes |
| 6,926,715 B1 | 8/2005 | Hauck et al. |
| 6,932,810 B2 | 8/2005 | Ryan |
| 6,945,978 B1 | 9/2005 | Hyde |
| 6,949,122 B2 | 9/2005 | Adams et al. |
| 6,966,914 B2 | 11/2005 | Abe |
| 6,986,775 B2 | 1/2006 | Morales et al. |
| 7,004,970 B2 | 2/2006 | Cauthen et al. |
| 7,011,669 B2 | 3/2006 | Kimblad |
| 7,033,390 B2 | 4/2006 | Johnson et al. |
| 7,048,754 B2 | 5/2006 | Martin et al. |
| 7,056,294 B2 * | 6/2006 | Khairkhahan ... A61B 17/32075 606/167 |
| 7,112,207 B2 | 9/2006 | Allen et al. |
| 7,226,467 B2 | 6/2007 | Lucatero et al. |
| 7,258,694 B1 | 8/2007 | Choi et al. |
| 7,288,097 B2 | 10/2007 | Seguin |
| 7,291,168 B2 | 11/2007 | Macoviak et al. |
| 7,338,467 B2 | 3/2008 | Lutter |
| 7,381,210 B2 | 6/2008 | Zarbatany et al. |
| 7,435,257 B2 | 10/2008 | Lashinski et al. |
| 7,464,712 B2 | 12/2008 | Oz et al. |
| 7,497,822 B1 | 3/2009 | Kugler et al. |
| 7,533,790 B1 | 5/2009 | Knodel et al. |
| 7,563,267 B2 | 7/2009 | Goldfarb et al. |
| 7,563,273 B2 | 7/2009 | Goldfarb et al. |
| 7,604,646 B2 | 10/2009 | Goldfarb et al. |
| 7,608,091 B2 | 10/2009 | Goldfarb et al. |
| 7,635,329 B2 | 12/2009 | Goldfarb et al. |
| 7,651,502 B2 | 1/2010 | Jackson |
| 7,655,015 B2 | 2/2010 | Goldfarb et al. |
| 7,666,204 B2 | 2/2010 | Thornton et al. |
| 7,955,340 B2 | 6/2011 | Michlitsch et al. |
| 8,216,234 B2 | 7/2012 | Long |
| 8,257,356 B2 | 9/2012 | Bleich et al. |
| 8,398,708 B2 | 3/2013 | Meiri et al. |
| 8,435,237 B2 | 5/2013 | Bahney |
| 8,496,655 B2 | 7/2013 | Epp et al. |
| 8,500,768 B2 | 8/2013 | Cohen |
| 8,523,881 B2 | 9/2013 | Cabiri et al. |
| 8,623,077 B2 | 1/2014 | Cohn |
| 8,690,858 B2 | 4/2014 | Machold et al. |
| 8,821,518 B2 | 9/2014 | Saliman et al. |
| 8,926,588 B2 | 1/2015 | Berthiaume et al. |
| 9,126,032 B2 | 9/2015 | Khairkhahan et al. |
| 9,211,119 B2 | 12/2015 | Hendricksen et al. |
| 9,370,341 B2 | 6/2016 | Ceniccola et al. |
| 9,498,331 B2 | 11/2016 | Chang et al. |
| 9,572,666 B2 | 2/2017 | Basude et al. |
| 9,770,256 B2 | 9/2017 | Cohen et al. |
| 9,949,833 B2 | 4/2018 | McCleary et al. |
| 10,238,493 B1 * | 3/2019 | Metchik ............. A61F 2/2466 |
| 10,667,804 B2 | 6/2020 | Basude et al. |
| 11,013,554 B2 | 5/2021 | Coates |
| 11,406,250 B2 | 8/2022 | Saadat et al. |
| 2001/0002445 A1 | 5/2001 | Vesely |
| 2001/0004715 A1 | 6/2001 | Duran et al. |
| 2001/0005787 A1 | 6/2001 | Oz et al. |
| 2001/0010005 A1 | 7/2001 | Kammerer et al. |
| 2001/0018611 A1 | 8/2001 | Solem et al. |
| 2001/0022872 A1 | 9/2001 | Marui |
| 2001/0037084 A1 | 11/2001 | Nardeo |
| 2001/0039411 A1 | 11/2001 | Johansson et al. |
| 2001/0044568 A1 | 11/2001 | Langberg et al. |
| 2001/0044635 A1 | 11/2001 | Niizeki et al. |
| 2002/0013547 A1 | 1/2002 | Paskar |
| 2002/0013571 A1 | 1/2002 | Goldfarb et al. |
| 2002/0022848 A1 | 2/2002 | Garrison et al. |
| 2002/0026233 A1 | 2/2002 | Shaknovich |
| 2002/0035361 A1 | 3/2002 | Houser et al. |
| 2002/0035381 A1 | 3/2002 | Bardy et al. |
| 2002/0042651 A1 | 4/2002 | Liddicoat et al. |
| 2002/0055767 A1 | 5/2002 | Forde et al. |
| 2002/0055774 A1 | 5/2002 | Liddicoat |
| 2002/0055775 A1 | 5/2002 | Carpentier et al. |
| 2002/0058910 A1 | 5/2002 | Hermann et al. |
| 2002/0058995 A1 | 5/2002 | Stevens |
| 2002/0077687 A1 | 6/2002 | Ahn |
| 2002/0087148 A1 | 7/2002 | Brock et al. |
| 2002/0087169 A1 | 7/2002 | Brock et al. |
| 2002/0087173 A1 | 7/2002 | Alferness et al. |
| 2002/0103532 A1 | 8/2002 | Langberg et al. |
| 2002/0107534 A1 | 8/2002 | Schaefer et al. |
| 2002/0147456 A1 | 10/2002 | Diduch et al. |
| 2002/0156526 A1 | 10/2002 | Hlavka et al. |
| 2002/0158528 A1 | 10/2002 | Tsuzaki et al. |
| 2002/0161378 A1 | 10/2002 | Downing |
| 2002/0169360 A1 | 11/2002 | Taylor et al. |
| 2002/0173811 A1 | 11/2002 | Tu et al. |
| 2002/0173841 A1 | 11/2002 | Ortiz et al. |
| 2002/0183766 A1 | 12/2002 | Seguin |
| 2002/0183787 A1 | 12/2002 | Wahr et al. |
| 2002/0183835 A1 | 12/2002 | Taylor et al. |
| 2003/0005797 A1 | 1/2003 | Hopper et al. |
| 2003/0045778 A1 | 3/2003 | Ohline et al. |
| 2003/0050693 A1 | 3/2003 | Quijano et al. |
| 2003/0069570 A1 | 4/2003 | Witzel et al. |
| 2003/0069593 A1 | 4/2003 | Tremulis et al. |
| 2003/0069636 A1 | 4/2003 | Solem et al. |
| 2003/0074012 A1 | 4/2003 | Nguyen et al. |
| 2003/0078654 A1 | 4/2003 | Taylor et al. |
| 2003/0083742 A1 | 5/2003 | Spence et al. |
| 2003/0105519 A1 | 6/2003 | Fasol et al. |
| 2003/0105520 A1 | 6/2003 | Alferness et al. |
| 2003/0120340 A1 | 6/2003 | Liska et al. |
| 2003/0120341 A1 | 6/2003 | Shennib et al. |
| 2003/0130669 A1 | 7/2003 | Damarati |
| 2003/0130730 A1 | 7/2003 | Cohn et al. |

(56) References Cited

U.S. PATENT DOCUMENTS

| | | |
|---|---|---|
| 2003/0144697 A1 | 7/2003 | Mathis et al. |
| 2003/0167071 A1 | 9/2003 | Martin et al. |
| 2003/0171776 A1 | 9/2003 | Adams et al. |
| 2003/0187467 A1 | 10/2003 | Schreck |
| 2003/0195562 A1 | 10/2003 | Collier et al. |
| 2003/0208231 A1 | 11/2003 | Williamson et al. |
| 2003/0229395 A1 | 12/2003 | Cox |
| 2003/0233038 A1 | 12/2003 | Hassett |
| 2004/0002719 A1 | 1/2004 | Oz et al. |
| 2004/0003819 A1 | 1/2004 | St et al. |
| 2004/0015232 A1 | 1/2004 | Shu et al. |
| 2004/0019377 A1 | 1/2004 | Taylor et al. |
| 2004/0019378 A1 | 1/2004 | Hlavka et al. |
| 2004/0024414 A1 | 2/2004 | Downing |
| 2004/0030319 A1* | 2/2004 | Korkor ............ A61M 25/0074 604/506 |
| 2004/0030382 A1 | 2/2004 | St et al. |
| 2004/0034380 A1 | 2/2004 | Woolfson et al. |
| 2004/0039442 A1 | 2/2004 | St et al. |
| 2004/0039443 A1 | 2/2004 | Solem et al. |
| 2004/0044350 A1 | 3/2004 | Martin et al. |
| 2004/0044365 A1 | 3/2004 | Bachman |
| 2004/0049207 A1 | 3/2004 | Goldfarb et al. |
| 2004/0049211 A1 | 3/2004 | Tremulis et al. |
| 2004/0059345 A1 | 3/2004 | Nakao et al. |
| 2004/0073302 A1 | 4/2004 | Rourke et al. |
| 2004/0078053 A1 | 4/2004 | Berg et al. |
| 2004/0087975 A1 | 5/2004 | Lucatero et al. |
| 2004/0088047 A1 | 5/2004 | Spence et al. |
| 2004/0092858 A1 | 5/2004 | Wilson et al. |
| 2004/0092962 A1 | 5/2004 | Thornton et al. |
| 2004/0097878 A1 | 5/2004 | Anderson et al. |
| 2004/0097979 A1 | 5/2004 | Svanidze et al. |
| 2004/0106989 A1 | 6/2004 | Wilson et al. |
| 2004/0111099 A1 | 6/2004 | Nguyen et al. |
| 2004/0116848 A1 | 6/2004 | Gardeski et al. |
| 2004/0116951 A1 | 6/2004 | Rosengart |
| 2004/0122448 A1 | 6/2004 | Levine |
| 2004/0127849 A1 | 7/2004 | Kantor |
| 2004/0127981 A1 | 7/2004 | Rahdert et al. |
| 2004/0127982 A1 | 7/2004 | Machold et al. |
| 2004/0127983 A1 | 7/2004 | Mortier et al. |
| 2004/0133062 A1 | 7/2004 | Pai et al. |
| 2004/0133063 A1 | 7/2004 | McCarthy et al. |
| 2004/0133082 A1 | 7/2004 | Abraham-Fuchs et al. |
| 2004/0133192 A1 | 7/2004 | Houser et al. |
| 2004/0133220 A1 | 7/2004 | Lashinski et al. |
| 2004/0133232 A1 | 7/2004 | Rosenbluth et al. |
| 2004/0133240 A1 | 7/2004 | Adams et al. |
| 2004/0133273 A1 | 7/2004 | Cox |
| 2004/0138744 A1 | 7/2004 | Lashinski et al. |
| 2004/0138745 A1 | 7/2004 | Macoviak et al. |
| 2004/0147826 A1 | 7/2004 | Peterson |
| 2004/0148021 A1 | 7/2004 | Cartledge et al. |
| 2004/0152847 A1 | 8/2004 | Emri et al. |
| 2004/0152947 A1 | 8/2004 | Schroeder et al. |
| 2004/0153144 A1 | 8/2004 | Seguin |
| 2004/0158123 A1 | 8/2004 | Jayaraman |
| 2004/0162610 A1 | 8/2004 | Liska et al. |
| 2004/0167539 A1 | 8/2004 | Kuehn et al. |
| 2004/0186486 A1 | 9/2004 | Roue et al. |
| 2004/0186566 A1 | 9/2004 | Hindrichs et al. |
| 2004/0193191 A1 | 9/2004 | Starksen et al. |
| 2004/0215339 A1 | 10/2004 | Drasler et al. |
| 2004/0220593 A1 | 11/2004 | Greenhalgh |
| 2004/0220657 A1 | 11/2004 | Nieminen et al. |
| 2004/0225233 A1 | 11/2004 | Frankowski et al. |
| 2004/0225300 A1 | 11/2004 | Goldfarb et al. |
| 2004/0225305 A1 | 11/2004 | Ewers et al. |
| 2004/0225353 A1 | 11/2004 | McGuckin et al. |
| 2004/0236354 A1 | 11/2004 | Seguin |
| 2004/0242960 A1 | 12/2004 | Orban |
| 2004/0243229 A1 | 12/2004 | Vidlund et al. |
| 2004/0249452 A1 | 12/2004 | Adams et al. |
| 2004/0249453 A1 | 12/2004 | Cartledge et al. |
| 2004/0260393 A1 | 12/2004 | Rahdert et al. |
| 2005/0004583 A1 | 1/2005 | Oz et al. |
| 2005/0004665 A1 | 1/2005 | Aklog |
| 2005/0004668 A1 | 1/2005 | Aklog et al. |
| 2005/0021056 A1 | 1/2005 | St et al. |
| 2005/0021057 A1 | 1/2005 | St et al. |
| 2005/0021058 A1 | 1/2005 | Negro |
| 2005/0033446 A1 | 2/2005 | Deem et al. |
| 2005/0038383 A1 | 2/2005 | Kelley et al. |
| 2005/0038508 A1 | 2/2005 | Gabbay |
| 2005/0049698 A1 | 3/2005 | Bolling et al. |
| 2005/0055089 A1 | 3/2005 | Macoviak et al. |
| 2005/0059351 A1 | 3/2005 | Cauwels et al. |
| 2005/0065453 A1 | 3/2005 | Shabaz et al. |
| 2005/0085903 A1 | 4/2005 | Lau |
| 2005/0119735 A1 | 6/2005 | Spence et al. |
| 2005/0131438 A1 | 6/2005 | Cohn |
| 2005/0143809 A1 | 6/2005 | Salahieh et al. |
| 2005/0149014 A1 | 7/2005 | Hauck et al. |
| 2005/0159763 A1 | 7/2005 | Mollenauer et al. |
| 2005/0159810 A1 | 7/2005 | Filsoufi |
| 2005/0192633 A1 | 9/2005 | Montpetit |
| 2005/0197694 A1 | 9/2005 | Pai et al. |
| 2005/0197695 A1 | 9/2005 | Stacchino et al. |
| 2005/0216039 A1 | 9/2005 | Lederman |
| 2005/0228422 A1 | 10/2005 | Machold et al. |
| 2005/0228495 A1 | 10/2005 | Macoviak |
| 2005/0251001 A1 | 11/2005 | Hassett |
| 2005/0256452 A1 | 11/2005 | Demarchi et al. |
| 2005/0267493 A1 | 12/2005 | Schreck et al. |
| 2005/0273160 A1 | 12/2005 | Lashinski et al. |
| 2005/0277876 A1 | 12/2005 | Hayden |
| 2005/0287493 A1 | 12/2005 | Novak et al. |
| 2006/0004247 A1 | 1/2006 | Kute et al. |
| 2006/0009759 A1 | 1/2006 | Chrisitian et al. |
| 2006/0015003 A1 | 1/2006 | Moaddes et al. |
| 2006/0015179 A1 | 1/2006 | Bulman-Fleming et al. |
| 2006/0020275 A1 | 1/2006 | Goldfarb et al. |
| 2006/0020327 A1 | 1/2006 | Lashinski et al. |
| 2006/0020334 A1* | 1/2006 | Lashinski ............... A61F 2/014 623/2.11 |
| 2006/0030866 A1 | 2/2006 | Schreck |
| 2006/0030867 A1 | 2/2006 | Zadno |
| 2006/0030885 A1 | 2/2006 | Hyde |
| 2006/0058871 A1 | 3/2006 | Zakay et al. |
| 2006/0064115 A1 | 3/2006 | Allen et al. |
| 2006/0064116 A1 | 3/2006 | Allen et al. |
| 2006/0064118 A1 | 3/2006 | Kimblad |
| 2006/0074484 A1 | 4/2006 | Huber |
| 2006/0089671 A1 | 4/2006 | Goldfarb et al. |
| 2006/0089711 A1 | 4/2006 | Dolan |
| 2006/0135961 A1 | 6/2006 | Rosenman et al. |
| 2006/0135993 A1 | 6/2006 | Seguin |
| 2006/0184198 A1 | 8/2006 | Bales et al. |
| 2006/0184203 A1 | 8/2006 | Martin et al. |
| 2006/0195012 A1 | 8/2006 | Mortier et al. |
| 2006/0229708 A1 | 10/2006 | Powell et al. |
| 2006/0252984 A1 | 11/2006 | Rahdert et al. |
| 2006/0276890 A1 | 12/2006 | Solem et al. |
| 2007/0016225 A1 | 1/2007 | Nakao |
| 2007/0038293 A1 | 2/2007 | St et al. |
| 2007/0060997 A1 | 3/2007 | de Boer |
| 2007/0073185 A1 | 3/2007 | Nakao |
| 2007/0100356 A1 | 5/2007 | Lucatero et al. |
| 2007/0118155 A1 | 5/2007 | Goldfarb et al. |
| 2007/0129737 A1 | 6/2007 | Goldfarb et al. |
| 2007/0173757 A1 | 7/2007 | Levine et al. |
| 2007/0197858 A1 | 8/2007 | Goldfarb et al. |
| 2007/0198082 A1 | 8/2007 | Kapadia et al. |
| 2007/0260225 A1 | 11/2007 | Sakakine et al. |
| 2007/0287884 A1 | 12/2007 | Schena |
| 2008/0009858 A1 | 1/2008 | Rizvi |
| 2008/0039935 A1 | 2/2008 | Buch et al. |
| 2008/0045936 A1 | 2/2008 | Vaska et al. |
| 2008/0051703 A1 | 2/2008 | Thornton et al. |
| 2008/0051807 A1 | 2/2008 | St et al. |
| 2008/0097467 A1 | 4/2008 | Gruber et al. |
| 2008/0097489 A1 | 4/2008 | Goldfarb et al. |
| 2008/0167714 A1 | 7/2008 | St et al. |

(56) References Cited

U.S. PATENT DOCUMENTS

| | | |
|---|---|---|
| 2008/0183194 A1 | 7/2008 | Goldfarb et al. |
| 2008/0188850 A1 | 8/2008 | Mody et al. |
| 2008/0195126 A1 | 8/2008 | Solem |
| 2008/0243249 A1 | 10/2008 | Kohm et al. |
| 2008/0294175 A1 | 11/2008 | Bardsley et al. |
| 2008/0312496 A1 | 12/2008 | Zwolinski |
| 2009/0012538 A1 | 1/2009 | Saliman et al. |
| 2009/0036768 A1 | 2/2009 | Seehusen et al. |
| 2009/0156995 A1 | 6/2009 | Martin et al. |
| 2009/0163934 A1 | 6/2009 | Raschdorf et al. |
| 2009/0177266 A1 | 7/2009 | Powell et al. |
| 2009/0192510 A1 | 7/2009 | Bahney |
| 2009/0198322 A1 | 8/2009 | Deem et al. |
| 2009/0204005 A1 | 8/2009 | Keast et al. |
| 2009/0209955 A1 | 8/2009 | Forster et al. |
| 2009/0209991 A1 | 8/2009 | Hinchliffe et al. |
| 2009/0270858 A1 | 10/2009 | Hauck et al. |
| 2009/0276039 A1 | 11/2009 | Meretei |
| 2009/0281619 A1 | 11/2009 | Le et al. |
| 2009/0326567 A1 | 12/2009 | Goldfarb et al. |
| 2010/0016958 A1 | 1/2010 | St et al. |
| 2010/0022823 A1 | 1/2010 | Goldfarb et al. |
| 2010/0044410 A1 | 2/2010 | Argentine et al. |
| 2010/0121437 A1 | 5/2010 | Subramanian et al. |
| 2010/0152612 A1 | 6/2010 | Headley et al. |
| 2010/0217261 A1 | 8/2010 | Watson |
| 2010/0262231 A1 | 10/2010 | Tuval et al. |
| 2010/0268226 A1 | 10/2010 | Epp et al. |
| 2010/0298929 A1 | 11/2010 | Thornton et al. |
| 2011/0009864 A1 | 1/2011 | Bucciaglia et al. |
| 2011/0184405 A1 | 7/2011 | Mueller |
| 2011/0224710 A1 | 9/2011 | Bleich |
| 2011/0238052 A1 | 9/2011 | Robinson |
| 2011/0282250 A1 | 11/2011 | Fung et al. |
| 2012/0022527 A1 | 1/2012 | Woodruff et al. |
| 2012/0022640 A1 | 1/2012 | Gross et al. |
| 2012/0065464 A1 | 3/2012 | Ellis et al. |
| 2012/0150194 A1 | 6/2012 | Odermatt et al. |
| 2012/0157765 A1* | 6/2012 | Mitelberg .............. A61B 1/018 606/147 |
| 2012/0172915 A1 | 7/2012 | Fifer et al. |
| 2012/0179184 A1 | 7/2012 | Orlov |
| 2012/0265222 A1 | 10/2012 | Gordin et al. |
| 2012/0310330 A1 | 12/2012 | Buchbinder et al. |
| 2012/0316639 A1 | 12/2012 | Kleinschrodt |
| 2012/0330348 A1 | 12/2012 | Strauss et al. |
| 2013/0041314 A1 | 2/2013 | Dillon |
| 2013/0066341 A1 | 3/2013 | Ketai et al. |
| 2013/0066342 A1 | 3/2013 | Dell et al. |
| 2013/0109910 A1 | 5/2013 | Alexander et al. |
| 2013/0172828 A1 | 7/2013 | Kappel et al. |
| 2013/0317515 A1 | 11/2013 | Kuroda et al. |
| 2014/0039511 A1 | 2/2014 | Morris et al. |
| 2014/0135799 A1 | 5/2014 | Henderson |
| 2014/0228871 A1* | 8/2014 | Cohen .............. A61B 17/32053 606/170 |
| 2014/0276913 A1 | 9/2014 | Tah et al. |
| 2014/0309670 A1 | 10/2014 | Bakos et al. |
| 2014/0324164 A1 | 10/2014 | Gross et al. |
| 2014/0350662 A1 | 11/2014 | Vaturi |
| 2014/0358224 A1 | 12/2014 | Tegels et al. |
| 2014/0364866 A1 | 12/2014 | Dryden et al. |
| 2014/0379074 A1 | 12/2014 | Spence et al. |
| 2015/0005704 A1 | 1/2015 | Heisel et al. |
| 2015/0005801 A1 | 1/2015 | Marquis et al. |
| 2015/0051698 A1 | 2/2015 | Ruyra et al. |
| 2015/0094800 A1 | 4/2015 | Chawla |
| 2015/0112430 A1 | 4/2015 | Creaven et al. |
| 2015/0211946 A1 | 7/2015 | Pons et al. |
| 2015/0230947 A1 | 8/2015 | Krieger et al. |
| 2015/0257877 A1 | 9/2015 | Hernandez |
| 2015/0257883 A1* | 9/2015 | Basude .............. A61B 17/0682 623/2.11 |
| 2015/0306806 A1 | 10/2015 | Dando et al. |
| 2015/0313581 A1 | 11/2015 | Wolfe et al. |
| 2016/0015410 A1 | 1/2016 | Asirvatham et al. |
| 2016/0074165 A1 | 3/2016 | Spence et al. |
| 2016/0174979 A1 | 6/2016 | Wei |
| 2016/0317174 A1* | 11/2016 | Dake .............. A61B 17/320016 |
| 2017/0042678 A1 | 2/2017 | Ganesan et al. |
| 2017/0100183 A1 | 4/2017 | Iaizzo et al. |
| 2017/0143330 A1 | 5/2017 | Basude et al. |
| 2017/0202559 A1 | 7/2017 | Taha |
| 2017/0232238 A1 | 8/2017 | Biller et al. |
| 2018/0008268 A1* | 1/2018 | Khairkhahan ......... A61B 17/10 |
| 2018/0028215 A1 | 2/2018 | Cohen |
| 2018/0092661 A1* | 4/2018 | Prabhu .................. A61B 18/24 |
| 2018/0133010 A1 | 5/2018 | Kizuka |
| 2018/0161159 A1 | 6/2018 | Lee et al. |
| 2018/0360457 A1 | 12/2018 | Ellis et al. |
| 2019/0029790 A1 | 1/2019 | Bak-Boychuk et al. |
| 2019/0183571 A1 | 6/2019 | De Marchena |
| 2019/0298517 A1 | 10/2019 | Sanchez et al. |
| 2019/0307458 A1 | 10/2019 | Mathis et al. |
| 2020/0121460 A1 | 4/2020 | Dale et al. |
| 2021/0113232 A1 | 4/2021 | Ortiz et al. |
| 2021/0145574 A1 | 5/2021 | Childs et al. |

FOREIGN PATENT DOCUMENTS

| | | |
|---|---|---|
| CN | 103841899 A | 6/2014 |
| CN | 104244841 A | 12/2014 |
| DE | 3504292 C1 | 7/1986 |
| DE | 9100873 U1 | 4/1991 |
| DE | 10116168 A1 | 11/2001 |
| EP | 0179562 A1 | 4/1986 |
| EP | 0558031 A2 | 9/1993 |
| EP | 0684012 A2 | 11/1995 |
| EP | 0727239 A2 | 8/1996 |
| EP | 0782836 A1 | 7/1997 |
| EP | 1230899 A1 | 8/2002 |
| EP | 1674040 A2 | 6/2006 |
| EP | 1980288 A1 | 10/2008 |
| EP | 2005912 A2 | 12/2008 |
| EP | 2537487 A1 | 12/2012 |
| EP | 2641570 A1 | 9/2013 |
| EP | 2702965 A1 | 3/2014 |
| EP | 2740419 A1 | 6/2014 |
| EP | 3009103 A1 | 4/2016 |
| FR | 2705556 A1 | 12/1994 |
| FR | 2768324 A1 | 3/1999 |
| FR | 2903292 A1 | 1/2008 |
| GB | 1598111 A | 9/1981 |
| GB | 2151142 A | 7/1985 |
| JP | 09-253030 A | 9/1997 |
| JP | 11-089937 A | 4/1999 |
| JP | 2000-283130 A | 10/2000 |
| JP | 2001-517529 A | 10/2001 |
| JP | 2006-528911 A | 12/2006 |
| JP | 2013-516244 A | 5/2013 |
| JP | 2013-523384 A | 6/2013 |
| JP | 2014-523274 A | 9/2014 |
| JP | 2015-502548 A | 1/2015 |
| JP | 2018-030008 A | 3/2018 |
| WO | 81/00668 A1 | 3/1981 |
| WO | 91/01689 A1 | 2/1991 |
| WO | 91/18881 A1 | 12/1991 |
| WO | 92/12690 A1 | 8/1992 |
| WO | 94/18881 A1 | 9/1994 |
| WO | 94/18893 A1 | 9/1994 |
| WO | 95/08292 A1 | 3/1995 |
| WO | 95/11620 A2 | 5/1995 |
| WO | 95/15715 A1 | 6/1995 |
| WO | 96/14032 A1 | 5/1996 |
| WO | 96/20655 A1 | 7/1996 |
| WO | 96/22735 A1 | 8/1996 |
| WO | 96/30072 A1 | 10/1996 |
| WO | 97/18746 A2 | 5/1997 |
| WO | 97/25927 A1 | 7/1997 |
| WO | 97/26034 A1 | 7/1997 |
| WO | 97/38748 A2 | 10/1997 |
| WO | 97/39688 A2 | 10/1997 |
| WO | 97/48436 A2 | 12/1997 |
| WO | 98/07375 A1 | 2/1998 |

(56) References Cited

FOREIGN PATENT DOCUMENTS

| | | |
|---|---|---|
| WO | 98/24372 A1 | 6/1998 |
| WO | 98/30153 A1 | 7/1998 |
| WO | 98/32382 A1 | 7/1998 |
| WO | 98/35638 A1 | 8/1998 |
| WO | 99/00059 A1 | 1/1999 |
| WO | 99/01377 A1 | 1/1999 |
| WO | 99/07295 A1 | 2/1999 |
| WO | 99/07354 A2 | 2/1999 |
| WO | 99/13777 A1 | 3/1999 |
| WO | 99/44524 A2 | 9/1999 |
| WO | 99/66967 A1 | 12/1999 |
| WO | 00/02489 A1 | 1/2000 |
| WO | 00/03651 A1 | 1/2000 |
| WO | 00/03759 A2 | 1/2000 |
| WO | 00/12168 A1 | 3/2000 |
| WO | 00/44313 A1 | 8/2000 |
| WO | 00/59382 A1 | 10/2000 |
| WO | 00/60995 A2 | 10/2000 |
| WO | 01/00111 A1 | 1/2001 |
| WO | 01/00114 A1 | 1/2001 |
| WO | 01/03651 A2 | 1/2001 |
| WO | 01/26557 A1 | 4/2001 |
| WO | 01/26586 A1 | 4/2001 |
| WO | 01/26587 A1 | 4/2001 |
| WO | 01/26588 A2 | 4/2001 |
| WO | 01/26703 A1 | 4/2001 |
| WO | 01/28432 A1 | 4/2001 |
| WO | 01/28455 A1 | 4/2001 |
| WO | 01/47438 A1 | 7/2001 |
| WO | 01/49213 A2 | 7/2001 |
| WO | 01/50985 A1 | 7/2001 |
| WO | 01/54618 A1 | 8/2001 |
| WO | 01/56512 A1 | 8/2001 |
| WO | 01/66001 A2 | 9/2001 |
| WO | 01/70320 A1 | 9/2001 |
| WO | 01/89440 A2 | 11/2001 |
| WO | 01/95831 A2 | 12/2001 |
| WO | 01/95832 A2 | 12/2001 |
| WO | 01/97741 A2 | 12/2001 |
| WO | 02/00099 A2 | 1/2002 |
| WO | 02/01999 A2 | 1/2002 |
| WO | 02/03892 A1 | 1/2002 |
| WO | 02/34167 A2 | 5/2002 |
| WO | 02/60352 | 8/2002 |
| WO | 02/62263 | 8/2002 |
| WO | 02/62270 | 8/2002 |
| WO | 02/62408 | 8/2002 |
| WO | 03/01893 A2 | 1/2003 |
| WO | 03/03930 | 1/2003 |
| WO | 03/20179 | 3/2003 |
| WO | 03/28558 A2 | 4/2003 |
| WO | 03/37171 | 5/2003 |
| WO | 03/47467 | 6/2003 |
| WO | 03/49619 | 6/2003 |
| WO | 03/73910 | 9/2003 |
| WO | 03/73913 | 9/2003 |
| WO | 03/82129 | 10/2003 |
| WO | 2003/105667 | 12/2003 |
| WO | 2004/004607 A1 | 1/2004 |
| WO | 2004/006810 A1 | 1/2004 |
| WO | 2004/012583 A2 | 2/2004 |
| WO | 2004/012789 A2 | 2/2004 |
| WO | 2004/014282 A2 | 2/2004 |
| WO | 2004/019811 A2 | 3/2004 |
| WO | 2004/030570 A2 | 4/2004 |
| WO | 2004/037317 A2 | 5/2004 |
| WO | 2004/045370 A2 | 6/2004 |
| WO | 2004/045378 A2 | 6/2004 |
| WO | 2004/045463 A2 | 6/2004 |
| WO | 2004/047679 A1 | 6/2004 |
| WO | 2004/062725 A1 | 7/2004 |
| WO | 2004/082523 A2 | 9/2004 |
| WO | 2004/082538 A2 | 9/2004 |
| WO | 2004/093730 A2 | 11/2004 |
| WO | 2004/103162 A2 | 12/2004 |
| WO | 2004/112585 A2 | 12/2004 |
| WO | 2004/112651 A2 | 12/2004 |
| WO | 2005/002424 A2 | 1/2005 |
| WO | 2005/018507 A2 | 3/2005 |
| WO | 2005/027797 A1 | 3/2005 |
| WO | 2005/032421 A2 | 4/2005 |
| WO | 2005/062931 A2 | 7/2005 |
| WO | 2005/112792 A2 | 12/2005 |
| WO | 2006/037073 A2 | 4/2006 |
| WO | 2006/105008 A1 | 10/2006 |
| WO | 2006/105009 A1 | 10/2006 |
| WO | 2006/113906 A1 | 10/2006 |
| WO | 2006/115875 A2 | 11/2006 |
| WO | 2006/115876 A2 | 11/2006 |
| WO | 2007/136829 A1 | 11/2007 |
| WO | 2008/103722 A2 | 8/2008 |
| WO | 2010/024801 A1 | 3/2010 |
| WO | 2010/121076 A2 | 10/2010 |
| WO | 2012/020521 A1 | 2/2012 |
| WO | 2013/049734 A1 | 4/2013 |
| WO | 2013/103934 A1 | 7/2013 |
| WO | 2014/064694 A2 | 5/2014 |
| WO | 2014/121280 A2 | 8/2014 |
| WO | 2016/022797 A1 | 2/2016 |
| WO | 2016/144708 A1 | 9/2016 |
| WO | 2016/150806 A1 | 9/2016 |
| WO | 2017/223073 A1 | 12/2017 |
| WO | 2018/009718 A1 | 1/2018 |
| WO | 2018/106482 A1 | 6/2018 |
| WO | 2018/236766 A1 | 12/2018 |
| WO | 2019/040943 A1 | 2/2019 |
| WO | 2019/195336 A1 | 10/2019 |

OTHER PUBLICATIONS

Langer et al., "Posterier mitral leaflet extensions: An adjunctive repair option for ischemic mitral regurgitation?" J Thorac Cardiovasc Surg, 131:868-877 (2006).

Lorusso et al., "The double-orifice technique for mitral valve reconstruction: predictors of postoperative outcome," Eur J. Cardiothorac Surg, 20:583-589 (2001).

Maisano et al, The Edge-to-edge Technique: A Simplified Method to Correct Mitral Insufficiency, Eur. J. Cardiothorac. Surg., Jan. 14, 1998, pp. 240-246, vol. 13.

Maisano et al, The future of transcatheter mitral valve interventions: competitive or complementary role of repair vs. replacement? Eur Heart J. Jul. 7, 2015; 36(26):1651-1659.

Maisano et al., "The double orifice repair for Barlow Disease: a simple solution for a complex repair," Supplement I Circulation, (Nov. 1999); 100(18):1-94.

Maisano et al., "The double orifice technique as a standardized approach to treat mitral regurgitation due to severe myxomatous disease: surgical technique," European Journal of Cardio-thoracic Surgery, 17:201-205 (2000).

Maisano et al., "The Future of Transcatheter Mitral Valve Interventions: Competitive or Complementary Role of Repair vs. Replacement?", Eur Heart J.36(26):1651-1659 ( Jul. 7, 2015 ).

Maisano et al., "The hemodynamic effects of double-orifice valve repair for mitral regurgitation: a 3D computational model," European Journal of Cardio-thoracic Surgery, 15:419-425 (1999).

Maisano et al., "Valve repair for traumatic tricuspid regurgitation," Eur. J. Cardio-thorac Surg, (1996) 10:867-873.

Mantovani et al., "Edge-to-edge Repair of Congenital Familiar Tricuspid Regurgitation: Case Report," J. Heart Valve Dis., 9:641-643 (2000).

McCarthy et al, "Tricuspid Valve Repair With the Cosgrove-Edwards Annuloplasty System", Ann. Thorac. Surg., 64:267-8 ( Jan. 16, 1997).

McCarthy et al., "Partial left ventriculectomy and mitral valve repair for end-stage congestive heart failure," European Journal of Cardio-thoracic Surgery, 13:337-343 (1998).

McCarthy et al., "Tricuspid Valve Repair With the Cosgrove-Edwards Annuloplasty System", Ann. Throac Surg. 64:267-8 (Jan. 16, 1997).

(56) References Cited

OTHER PUBLICATIONS

Moainie et al., "Correction of Traumatic Tricuspid Regurgitation Using the Double Orifice Technique," Annals of Thoracic Surgery, 73:963-965 (2002).
Morales et al., "Development of an Off Bypass Mitral Valve Repair," The Heart Surgery Forum #1999-4693, 2(2):115-120 (1999).
Nakanishi et al., "Early Outcome with the Alfieri Mitral Valve Repair," J. Cardiol., 37: 263-266 (2001) [Abstract in English; Article in Japanese].
Nielsen et al., "Edge-to-Edge Mitral Repair: Tension of the Approximating Suture and Leaflet Deformation During Acute Ischemic Mitral Regurgitation in the Ovine Heart," Circulation, 104(Suppl. 1):1-29-1-35 (2001).
Nishimura, et al. 2014 AHA/ACC guideline for the management of patients with valvular heart disease: executive summary: a report of the American College of Cardiology/American Heart Association Task Force on Practice Guidelines. J Am Coll Cardiol. Jun. 10, 2014;63(22):2438-88.
Noera et al., "Tricuspid Valve Incompetence Caused by Nonpenetrating Thoracic Trauma", Annals of Thoracic Surgery, 51:320-322 (1991).
Notice of Allowance received for U.S. Appl. No. 14/216,787, filed Nov. 7, 2016.
Notice of Allowance received for U.S. Appl. No. 14/216,787, mailed on Nov. 7, 2016.
Notice of Allowance received for U.S. Appl. No. 14/577,852, filed Apr. 25, 2018.
Notice of Allowance received for U.S. Appl. No. 14/577,852, mailed on Apr. 25, 2018.
Notice of Allowance received for U.S. Appl. No. 15/642,245, mailed on Jan. 29, 2020.
Notice of Allowance received for U.S. Appl. No. 15/642,245, mailed on Mar. 27, 2020.
Notice of Allowance received for U.S. Appl. No. 15/642,245, mailed on Nov. 6, 2019.
Notice of Allowance received for U.S. Appl. No. 15/423,060, mailed on Jan. 27, 2020.
Office Action received for U.S. Appl. No. 14/216,787, filed Apr. 8, 2016.
Office Action received for U.S. Appl. No. 14/216,787, mailed on Apr. 8, 2016.
Office Action received for U.S. Appl. No. 14/216,813, filed Apr. 6, 2018.
Office Action received for U.S. Appl. No. 14/216,813, filed Dec. 15, 2017.
Office Action received for U.S. Appl. No. 14/216,813, filed Mar. 9, 2017.
Office Action received for U.S. Appl. No. 14/216,813, mailed on Apr. 6, 2018.
Office Action received for U.S. Appl. No. 14/216,813, mailed on Dec. 15, 2017.
Office Action received for U.S. Appl. No. 14/216,813, mailed on Mar. 9, 2017.
Office Action received for U.S. Appl. No. 14/577,852, filed May 16, 2017.
Office Action received for U.S. Appl. No. 14/577,852, filed Oct. 20, 2016.
Office Action received for U.S. Appl. No. 14/577,852, filed Sep. 7, 2017.
Office Action received for U.S. Appl. No. 14/577,852, mailed on May 16, 2017.
Office Action received for U.S. Appl. No. 14/577,852, mailed on Oct. 20, 2016.
Office Action received for U.S. Appl. No. 14/577,852, mailed on Sep. 7, 2017.
Office Action received for U.S. Appl. No. 15/423,060, mailed on Apr. 25, 2019.
Office Action received for U.S. Appl. No. 15/423,060, mailed on Aug. 19, 2019.
Office Action received for U.S. Appl. No. 15/423,060, mailed on Oct. 28, 2019.
Office Action received for U.S. Appl. No. 15/642,245, mailed on Aug. 9, 2019.
Office Action received for U.S. Appl. No. 15/724,545, filed Dec. 27, 2019.
Office Action received for U.S. Appl. No. 15/724,545, mailed on Dec. 27, 2019.
Office Action received for U.S. Appl. No. 15/724,545, mailed on May 1, 2020.
Osawa et al., "Partial Left Ventriculectomy in a 3-Year Old Boy with Dilated Cardiomyopathy," Japanese Journal of Thoracic and Cardiovascular Surg, 48:590-593 (2000).
Park et al, Clinical Use of Blade Atrial Septostomy, Circulation, 1978, pp. 600-608, vol. 58.
Patel et al., #57 Epicardial Atrial Defibrillation: Novel Treatment of Postoperative Atrial Fibrillation, 2003 STS Presentation, [Abstract Only].
Privitera et al., "Alfieri Mitral Valve Repair: Clinical Outcome and Pathology," Circulation, 106:e173-e174 (2002).
Redaelli et al., "A Computational Study of the Hemodynamics After 'Edge-To-Edge' Mitral Valve Repair," Journal of Biomechanical Engineering, 123:565-570 (2001).
Reul et al., "Mitral Valve Reconstruction for Mitral Insufficiency," Progress in Cardiovascular Diseases, XXXIX(6):567-599 (1997).
Ricchi et al, Linear Segmental Annuloplasty for Mitral Valve Repair, Ann. Thorac. Surg., Jan. 7, 1997, pp. 1805-1806, vol. 63.
Robicsek et al., #60 The Bicuspid Aortic Valve: How Does It Function? Why Does It Fail? 2003 STS Presentation, [Abstract Only].
Rose et al., "Late MitraClip Failure: Removal Technique for Leaflet-Sparing Mitral Valve Repair", Journal of Cardiac Surgery, (Jul. 4, 2012), XP055047339, DOI: 10.1111/j. 1540-8191.2012.01483.x [retrieved on Dec. 11, 2012].
Supplemental European Search Report of EP Application No. 02746781, dated May 13, 2008, 3 pages total.
Supplementary European Search Report issued in European Application No. 05753261.6 dated Jun. 9, 2011, 3 pages total.
Tager et al, Long-Term Follow-Up of Rheumatic Patients Undergoing Left-Sided Valve Replacement With Tricuspid Annuloplasty—Validity of Preoperative Echocardiographic Criteria in the Decision to Perform Tricuspid Annuloplasty, Am. J. Cardiol., Apr. 15, 1998, pp. 1013-1016, vol. 81.
Takizawa H et al: Development of a microfine active bending catheter equipped with MIF tactile sensors", Micro Electro Mechanical Systems, 1999. MEMS '99. Twelfth IEEE Interna Tional Conference on Orlando, FL, USA Jan. 17-21, 1999, Piscataway, NJ, USA,IEEE, US, Jan. 17, 1999 (Jan. 17, 1999), pp. 412-417, XP010321677, ISBN: 978-0-7803-5194-3 figures 1-3.".
Tamura et al., "Edge to Edge Repair for Mitral Regurgitation in a Patient with Chronic Hemodialysis: Report of a Case," Kyobu Geka. The Japanese Journal of Thoracic Surgery, 54(9):788-790 (2001).
Tibayan et al., #59 Annular Geometric Remodeling in Chronic Ischemic Mitral Regurgitation, 2003 STS Presentation, [Abstract Only].
Timek et al., "Edge-to-edge mitral repair: gradients and three-dimensional annular dynamics in vivo during inotropic stimulation," Eur J. of Cardiothoracic Surg., 19:431-437 (2001).
Timek, "Edge-to-Edge Mitral Valve Repair without Annuloplasty Ring in Acute Ischemic Mitral Regurgitation," [Abstract] Clinical Science, Abstracts from Scientific Sessions, 106(19):2281 (2002).
Totaro, "Mitral valve repair for isolated prolapse of the anterior leaflet: an 11-year follow-up," European Journal of Cardio-thoracic Surgery, 15:119-126 (1999).
U.S. Provisional Application Filed on Jul. 6, 2016, by Khairkhahan., U.S. Appl. No. 62/359,121.
U.S. Provisional Application Filed on Nov. 7, 2016, by Khairkhahan., U.S. Appl. No. 62/418,571.
U.S. Provisional Application Filed on Oct. 22, 2018, by Dale et al., U.S. Appl. No. 62/748,947.

(56) References Cited

OTHER PUBLICATIONS

Uchida et al., Percutaneous Cardiomyotomy and Valvulotomy with Angioscopic Guidance, Am. Heart J., Apr. 1991, pp. 1221-1224, vol. 121.
Umana et al, 'Bow-Tie' Mitral Valve Repair: An Adjuvant Technique for Ischemic Mitral Regurgitation, Ann. Thorac. Surg., May 12, 1998, pp. 1640-1646, vol. 66.
Umana et al., "'Bow-tie' Mitral Valve Repair Successfully Addresses Subvalvular Dysfunction in Ischemic Mitral Regurgitation," Surgical Forum, XLVIII:279-280 (1997).
U.S. Appl. No. 14/216,813, filed Mar. 17, 2014, Hernandez.
Votta et al., "3-D Computational Analysis of the Stress Distribution on the Leaflets after Edge-to-Edge Repair of Mitral Regurgitation," Journal of Heart Valve Disease, 11:810-822 (2002).
Abe et al, "De Vega's Annuloplasty for Acquired Tricuspid Disease: Early and Late Results in 110 Patients", Ann. Thorac. Surg., pp. 670-676, vol. 48 (Jan. 1989).
Abe et al., "Updated in 1996—De Vega's Annuloplasty for Acquired Tricuspid Disease: Early and Late Results in 110 Patients", Ann. Thorac. Surg., pp. 1876-1877, vol. 62 (1996).
Agricola et al., "Mitral Valve Reserve in Double Orifice Technique: an Exercise Echocardiographic Study," Journal of Heart Valve Disease, 11(5):637-643 (2002).
Alfieri et al., "An Effective Technique to Correct Anterior Mitral Leaflet Prolapse," J. Card Surg., 14:468-470 (1999).
Alfieri et al., "Novel Suture Device for Beating Heart Mitral Leaflet Approximation," Annals of Thoracic Surgery, 74:1488-1493 (2002).
Alfieri et al., "The double orifice technique in mitral valve repair: a simple solution for complex problems," Journal of Thoracic and Cardiovascular Surgery, 122:674-681 (2001).
Alfieri et al., "The Edge to Edge Technique," The European Association For Cardio-Thoracic Surgery, 14th Annual Meeting, Frankfurt/ Germany, Oct. 7-11, 2000, Post Graduate Courses, Book of Proceedings.
Alfieri, "The Edge-to-Edge Repair of the Mitral Valve," [Abstract] 6th Annual New Era Cardiac Care: Innovation & Technology, Heart Surgery Forum, (Jan. 2003) pp. 103.
Ali Khan et al, Blade Atrial Septostomy: Experience with the First 50 Procedures, Cathet. Cardiovasc. Diagn., Aug. 1991, pp. 257-262, vol. 23.
Alvarez et al, Repairing the Degenerative Mitral Valve: Ten to Fifteen-year Follow-up, Journal Thoracic of Cardiovascular Surgery, Aug. 1996, pp. 238-247, vol. 112, No. 2.
Arisi et al., "Mitral Valve Repair with Alfieri Technique in Mitral Regurgitation of Diverse Etiology: Early Echocardiographic Results," Circulation Supplement II, 104(17):3240 (2001).
Bach et al, Early Improvement in Congestive Heart Failure After Correction of Secondary Mitral Regurgitation in End-stage Cardiomyopathy, American Heart Journal, Jun. 1995, pp. 1165-1170, vol. 129, No. 6.
Bach et al, Improvement Following Correction of Secondary Mitral Regurgitation in End-stage Cardiomyopathy With Mitral Annuloplasty, Am. J. Cardiol., Oct. 15, 1996, pp. 966-969, vol. 78.
Bailey, "Mitral Regurgitation" in Surgery of the Heart, Chapter 20, pp. 686-737 (1955).
Bernal et al., "The Valve Racket: a new and different concept of atrioventricular valve repair," Eur. J. Cardio-thoracic Surgery 29:1026-1029 (2006).
Bhudia et al., "Edge-to-Edge (Alfieri) Mitral Repair: Results in Diverse Clinical Settings," Ann Thorac Surg, 77:1598-1606 (2004).
Bhudia, #58 Edge-to-edge mitral repair: a versatile mitral repair technique, 2003 STS Presentation, [Abstract Only], 2004.
Bolling et al, Surgery for Acquired Heart Disease: Early Outcome of Mitral Valve Reconstruction in Patients with End-stage Cardiomyopathy, Journal of Thoracic and Cariovascular Surgery, Apr. 1995, pp. 676-683, vol. 109, No. 4.
Borghetti et al., "Preliminary observations on haemodynamics during physiological stress conditions following 'double-orifice' mitral valve repair," European Journal of Cardio-thoracic Surgery, 20:262-269 (2001).
Castedo, "Edge-to-Edge Tricuspid Repair for Redeveloped Valve Incompetence after DeVega's Annuloplasty," Ann Thora Surg., 75:605-606 (2003).
Chinese Office Action issued in Chinese Application No. 200980158707.2 dated Sep. 9, 2013.
Communication dated Apr. 16, 2018 from the European Patent Office in counterpart European application No. 04752603.3.
Communication dated Apr. 28, 2017 issued by the European Patent Office in counterpart application No. 16196023.2.
Communication dated Jan. 26, 2017, from the European Patent Office in counterpart European application No. 16196023.2.
Communication dated May 8, 2017, from the European Patent Office in counterpart European Application No. 04752714.8.
Dang N C et al., "Surgical Revision After Percutaneous Mitral Valve Repair with a Clip: Initial Multicenter Experience", The Annals of Thracic Surgery, Elsevier, United States, vol. 80, No. 6, pp. 2338-2342, (Dec. 1, 2005), XP027732951, ISSN:0003-4975 [retrieved on Dec. 1, 2005].
Dec et al, Idiopathic Dilated Cardiomyopathy, The New England Journal of Medicine, Dec. 8, 1994, pp. 1564-1575, vol. 331, No. 23.
Dottori et al., "Echocardiographic imaging of the Alfieri type mitral valve repair," Ital. Heart J., 2(4):319-320 (2001).
Downing et al., "Beating heart mitral valve surgery: Preliminary model and methodology," Journal of Thoracic and Cardiovascular Surgery, 123(6):1141-1146 (2002).
Extended European Search Report, dated Oct. 17, 2014, issued in European Patent Application No. 06751584.1.
Falk et al., "Computer-Enhanced Mitral Valve Surgery: Toward a Total Endoscopic Procedure," Seminars in Thoracic and Cardiovascular Surgery, 11(3):244-249 (1999).
Feldman, et al. Randomized Comparison of Percutaneous Repair and Surgery for Mitral Regurgitation: 5-Year Results of Everest II. J Am Coll Cardiol. Dec. 29, 2015;66(25):2844- 2854.
Filsoufi et al., "Restoring Optimal Surface of Coaptation With a Mini Leaflet Prosthesis: A New Surgical Concept for the Correction of Mitral Valve Prolapse," Intl. Soc. for Minimally Invasive Cardiothoracic Surgery 1(4):186-87 (2006).
Frazier et al., #62 Early Clinical Experience with an Implantable, Intracardiac Circulatory Support Device: Operative Considerations and Physiologic Implications, 2003 STS Presentation, 1 page total. [Abstract Only].
Fucci et al, Improved Results with Mitral Valve Repair Using New Surgical Techniques, Eur. J. Cardiothorac. Surg., Nov. 1995, pp. 621-627, vol. 9.
Fundaro et al., "Chordal Plication and Free Edge Remodeling for Mitral Anterior Leaflet Prolapse Repair: 8-Year Follow-up," Annals of Thoracic Surgery, 72:1515-1519 (2001).
Garcia-Rinaldi et al., "Left Ventricular Volume Reduction and Reconstruction is Ischemic Cardiomyopathy," Journal of Cardiac Surgery, 14:199-210 (1999).
Gateliene, "Early and postoperative results results of metal and tricuspid valve insufficiency surgical treatment using edge-to-edge central coaptation procedure," (Oct. 2002) 38 (Suppl 2):172 175.
Gatti et al., "The edge to edge technique as a trick to rescue an imperfect mitral valve repair," Eur. J. Cardiothorac Surg, 22:817-820 (2002).
Gundry, "Facile mitral valve repair utilizing leaflet edge approximation: midterm results of the Alfieri figure of eight repair," Presented at the Meeting of the Western Thoracic Surgical Association, (1999).
Gupta et al., #61 Influence of Older Donor Grafts on Heart Transplant Survival: Lack of Recipient Effects, 2003 STS Presentation, [Abstract Only].
Ikeda et al., "Batista's Operation with Coronary Artery Bypass Grafting and Mitral Valve Plasty for Ischemic Dilated Cardiomyopathy," The Japanese Journal of Thoracic and Cardiovascular Surgery, 48:746-749 (2000).
Izzat et al., "Early Experience with Partial Left Ventriculectomy in the Asia-Pacific Region," Annuals of Thoracic Surgery, 67:1703-1707 (1999).
Kallner et al., "Transaortic Approach for the Alfieri Stitch," Ann Thorac Surg, 71:378-380 (2001).

(56) References Cited

OTHER PUBLICATIONS

Kameda et al, Annuloplasty for Severe Mitral Regurgitation Due to Dilated Cardiomyopathy, Ann. Thorac. Surg., 1996, pp. 1829-1832, vol. 61.

Kavarana et al., "Transaortic Repair of Mitral Regurgitation," The Heart Surgery Forum, #2000-2389, 3(1):24-28 (2000).

Kaza et al., "Ventricular Reconstruction Results in Improved Left Ventricular Function and Amelioration of Mitral Insufficiency," Annals of Surgery, 235(6):828-832 (2002).

Khan et al., "Blade Atrial Septostomy; Experience with the First 50 Procedures", Catheterization and Cardiovascular Diagnosis, 23:257-262 (1991).

Kherani et al., "The Edge-To-Edge Mitral Valve Repair: The Columbia Presbyterian Experience," Ann. Thorac. Surg., 78:73-76 (2004).

Kron et al., "Surgical Relocation of the Posterior Papillary Muscle in Chronic Ischemic Mitral Regurgitation," Annals. Of Thoracic Surgery, 74:600-601 (2002).

\* cited by examiner

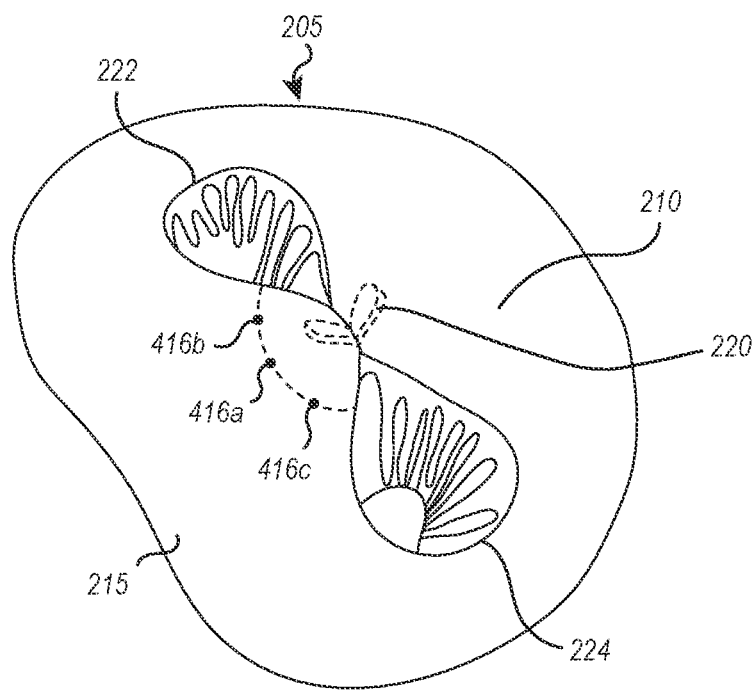
FIG. 4C
FIG. 4D
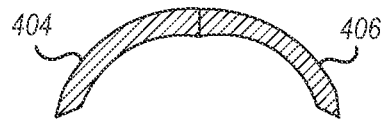
FIG. 4E
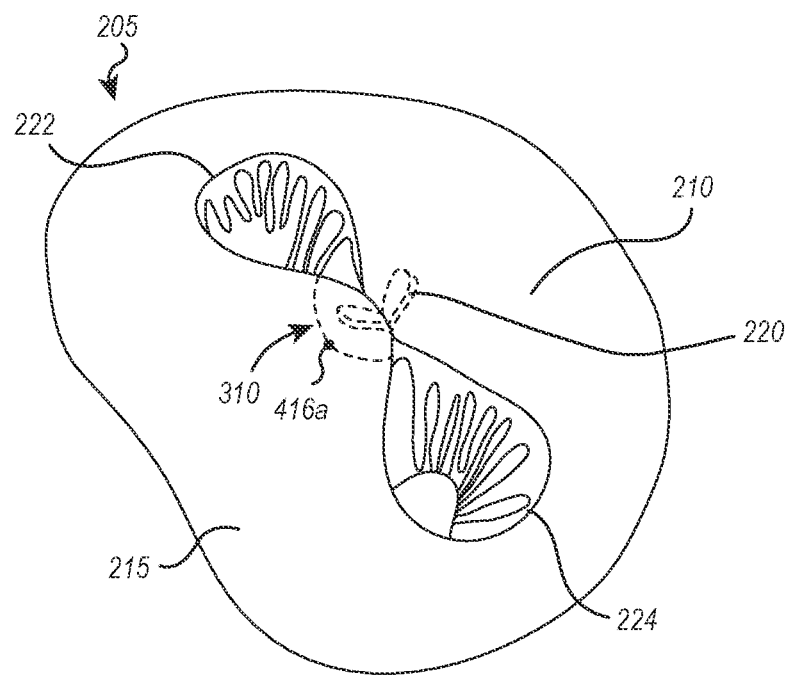
FIG. 4F

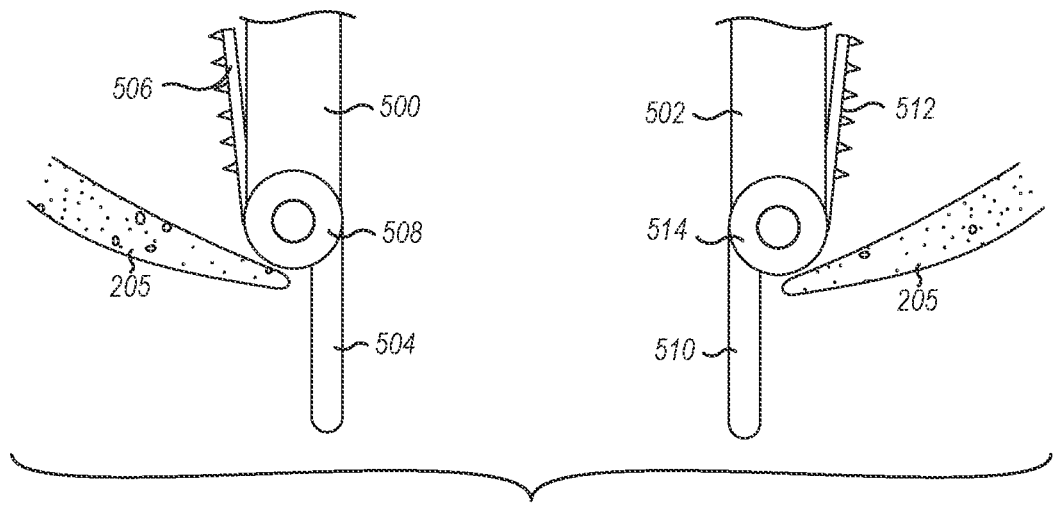
FIG. 5C
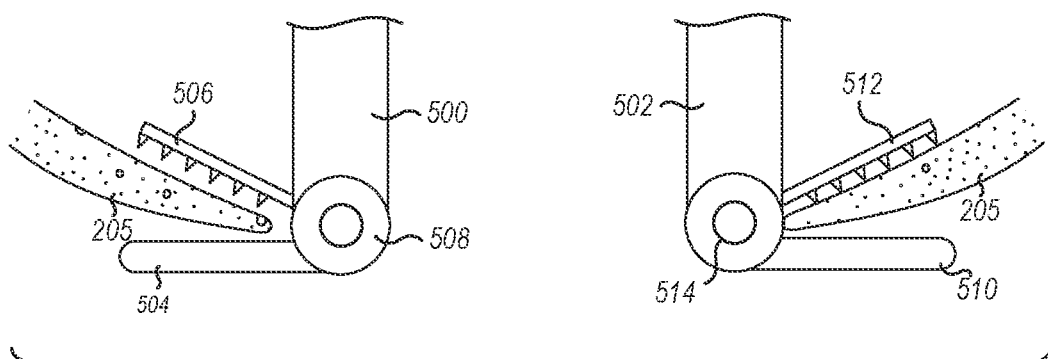
FIG. 5D
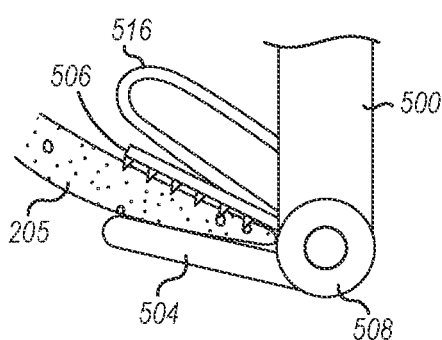 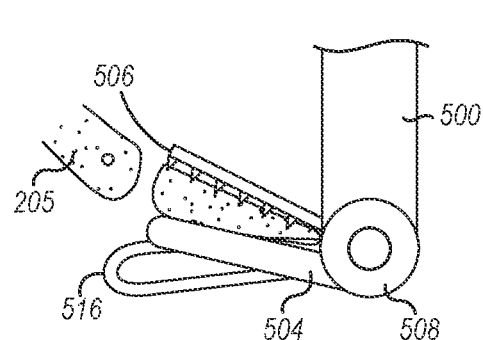
FIG. 5E　　　FIG. 5F

DEVICES AND METHODS FOR LEAFLET CUTTING

CROSS-REFERENCE TO RELATED APPLICATIONS

This application claims priority to U.S. Provisional Patent Application No. 63/020,669, filed May 6, 2020, the entire contents of which are incorporated by reference herein.

BACKGROUND OF THE INVENTION

The mitral valve controls blood flow from the left atrium to the left ventricle of the heart, preventing blood from flowing backwards from the left ventricle into the left atrium so that it is instead forced through the aortic valve for delivery of oxygenated blood throughout the body. A properly functioning mitral valve opens and closes to enable blood flow in one direction. However, in some circumstances the mitral valve is unable to close properly, allowing blood to regurgitate back into the atrium.

Mitral valve regurgitation has several causes. Functional mitral valve regurgitation is characterized by structurally normal mitral valve leaflets that are nevertheless unable to properly coapt with one another to close properly due to other structural deformations of surrounding heart structures. Other causes of mitral valve regurgitation are related to defects of the mitral valve leaflets, mitral valve annulus, or other mitral valve tissues.

The most common treatments for mitral valve regurgitation rely on valve replacement or repair including leaflet and annulus remodeling, the latter generally referred to as valve annuloplasty. One technique for mitral valve repair which relies on suturing adjacent segments of the opposed valve leaflets together is referred to as the "bowtie" or "edge-to-edge" technique. While these techniques can be effective, they usually rely on open heart surgery where the patient's chest is opened, typically via a sternotomy, and the patient is placed on cardiopulmonary bypass. The need to both, open the chest, and place the patient on bypass, is traumatic and has an associated high mortality and morbidity rate. In some patients, a fixation device can be installed into the heart using minimally invasive techniques. The fixation device can hold the adjacent segments of the opposed valve leaflets together and may reduce mitral valve regurgitation. One such device used to clip the anterior and posterior leaflets of the mitral valve together is the MitraClip® fixation device, sold by Abbott Vascular, Santa Clara, Calif., USA.

However, sometimes after a fixation device is installed, undesirable mitral valve regurgitation can still exist, or can arise again. For patients requiring re-intervention, the presence of a fixation device in their mitral valves obstructs transcatheter mitral valve replacement. These patients may also be considered too frail to tolerate open-heart surgery, so they are left with no viable options to further improve the function of their mitral valve.

Accordingly, it would be desirable to provide alternative and additional methods, devices, and systems for removing or disabling fixation devices that are already installed in preparation for the installation of an artificial, replacement mitral valve. The methods, devices, and systems may be useful for repair of tissues in the body other than heart valves. At least some of these objectives will be met by the invention described hereinbelow.

BRIEF SUMMARY OF THE INVENTION

Implementations of the present invention solve one or more problems in the art with systems, methods, and apparatus configured to cut leaflet tissue at a cardiac valve. The system may comprise a guide catheter having a proximal end and a distal end, wherein the distal end of the guide catheter is steerable to a position above a cardiac valve. The system may also include a handle coupled to the proximal end of the guide catheter, the handle comprising at least one control configured to steer the guide catheter to the position above the cardiac valve. Finally, the system may comprise a cutting mechanism, routable through the guide catheter and able to be positioned at the distal end of the guide catheter, configured to cut a portion of leaflet tissue of the cardiac valve.

A method for cutting leaflet tissue at a cardiac valve within a body may comprise positioning a guide catheter, having a proximal and a distal end such that the distal end of the guide catheter is positioned at a cardiac valve. The method may further comprise routing a cutting mechanism through the guide catheter such that the cutting mechanism extends to the distal end of the guide catheter, wherein the cardiac valve is associated with an interventional implant that approximates adjacent leaflets of the cardiac valve, and a cutting mechanism extends from the guide catheter. Also, the method may include positioning the hook catheter to place the cutting mechanism into contact with leaflet tissue located adjacent to the interventional implant and actuating the cutting mechanism to cut at a portion of least one leaflet of the approximated adjacent leaflet.

Additional features and advantages of exemplary implementations of the invention will be set forth in the description which follows, and in part will be obvious from the description, or may be learned by the practice of such exemplary implementations. The features and advantages of such implementations may be realized and obtained by means of the instruments and combinations particularly pointed out in the appended claims. These and other features will become more fully apparent from the following description and appended claims or may be learned by the practice of such exemplary implementations as set forth hereinafter.

BRIEF DESCRIPTION OF THE DRAWINGS

In order to describe the manner in which the above-recited and other advantages and features of the invention can be obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which:

FIGS. 4A-4F illustrate an alternative embodiment of a cutting mechanism according to the present disclosure;

FIGS. 5A-5J illustrate an alternative embodiment of a cutting mechanism according to the present disclosure shown in use in association with a cardiac valve;

DETAILED DESCRIPTION OF THE PREFERRED EMBODIMENTS

Implementations of the present invention solve one or more problems in the art with systems, methods, and apparatus configured to cut leaflet tissue at a cardiac valve. More specifically, at least one embodiment of the present invention, may comprise a guide catheter having a proximal end and a distal end, wherein the distal end of the guide catheter is steerable to a position above a cardiac valve. The system may also include a handle coupled to the proximal end of the guide catheter, the handle comprising at least one control configured to steer the guide catheter to the position above the cardiac valve. Finally, the system may comprise a cutting mechanism routable through the guide catheter and able to be positioned at the distal end of the guide catheter, the cutting mechanism configured to cut a portion of leaflet tissue of the cardiac valve.

Figure 1:
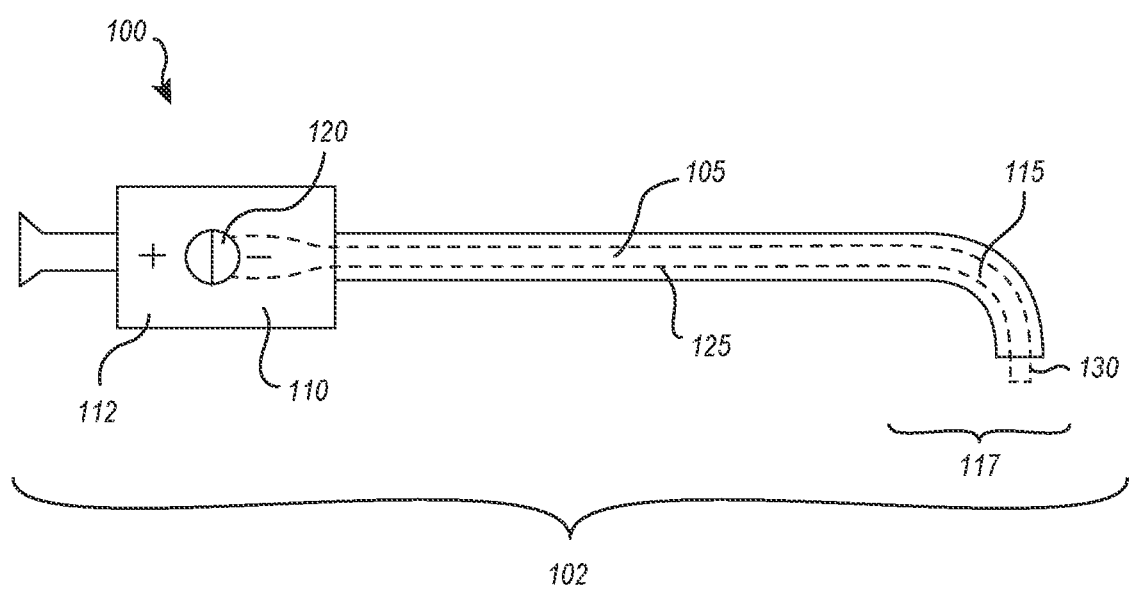
FIG. 1 illustrates an embodiment of a delivery system that may be utilized for guiding and/or delivering a cutting mechanism to a cardiac valve.

FIG. 1 illustrates an embodiment of a delivery system 100 that may be utilized for guiding and/or delivering a cutting mechanism to the cardiac valve. In at least one embodiment, the delivery system 100 includes a leaflet cutting system 100, which can include a delivery system 102 that may be utilized for guiding and/or delivering a cutting mechanism to the cardiac valve. The delivery system 102 can include a guide catheter 105 having a proximal end 112 and a distal end 115. The delivery system may comprise a handle 110 positioned on the proximal end 112 of the guide catheter 105. The guide catheter 105 may be operatively coupled to the handle 110. The guide catheter 105 may include a steerable portion 117 near the distal end 115 that can be steerable to enable the guiding and orienting of the guide catheter 105 through a patient's vasculature to a targeted treatment site, such as a mitral valve. For example, the handle 110 may include at least one control 120 (e.g., a dial, a switch, a slider, a button, etc.) that can be actuated to control the movement and curvature of a steerable portion 117 of the guide catheter 105.

In at least one embodiment, the at least one control 120 can be operatively coupled to one or more control lines 125 (e.g., pull wires) extending from the handle 110 through the guide catheter 105 to the distal end 115 of the guide catheter (e.g., through one or more lumens in the guide catheter 105). Actuation of the at least one control 120 may adjust the tensioning of one or more control lines 125 to steer the guide catheter 105 in a desired curvature and/or direction. FIG. 1 shows the handle 110 as having a single control 120 for providing steerability. Alternatively, a handle 110 may comprise more than one control 120 associated with any number of control lines.

While control lines or wires are described at various points in this application, it should be understood that references made throughout this application to control lines or wires may be a single wire or plurality of wires including or made of steel, titanium alloy, aluminum alloy, nickel alloy, other metals, a shape memory material (such as a shape memory alloy or shape memory polymer), inorganic polymer, organic polymer, ceramic, carbon materials, or other flexible material with sufficient tensile strength. For example, a control line 125 may be a steel cable. In another example, a control line 125 may be a monofilament suture. In another example, a control line 125 may be a multifilament suture. In yet another example, a control line 125 may be a braided suture.

It is desirable for guide catheter 105 to provide an adjustable distal end 115, which is capable of being positioned within a target body cavity in a desired orientation. Guide catheter 105 should have a large lumen diameter to accommodate the passage of a variety of devices, such as the various embodiments of the cutting mechanisms discussed hereinafter, and should have good wall strength to avoid kinking or collapse when bent around tight curves, and should have good column, tensile, and torsional strength to avoid deformation when the devices are passed through the lumen and torqued or translated. Guide catheter 105 should provide for a high degree of controlled deflection at its distal end 115, but should not take up significant lumen area to allow for passage of interventional devices, such as the cutting mechanisms discussed below. Further, guide catheter 105 should be able to be positioned in a manner which allows compound curves to be formed, for example curvature within more than one plane. Such manipulation should also allow fine control over distal end 115 to accommodate anatomical variations within the same type of body cavity and for use in different types of body cavities.

The guide catheter 105 may comprise a main body made of or including a flexible material. The main body may be made of or include a variety of flexible materials, such as thermoplastic elastomers (TPE). In some embodiments, the main body may be a polyether block amide (PEBA or PEBAX). The main body may have a constant durometer or may have varying durometer that varies along its longitudinal length or that varies in different portions of the body. For example, the main body of guide catheter 105 may be made of or include a body material having a durometer of 25D to 75D. In another example, the main body of guide catheter 105 may be made of or include a body material that has a durometer of about 45D. In at least one embodiment, the body material may include PEBAX 4533. In at least another embodiment, the body material may include PEBAX 3533.

The guide catheter 105 preferably defines a central lumen, extending axially through its entire length, through which other elongate elements, such as the cutting mechanisms may be inserted for accessing a treatment site. The central lumen may also include a central lumen lining on an inner surface thereof. In some embodiments, the central lumen lining may be a protective material that protects the interior walls from damage due to another element of the elongated member moving through or within the central lumen. In other embodiments, the central lumen lining may include a lubricious coating that reduces friction between the interior wall and another element of the elongated member moving through or within the central lumen. The central lumen lining may include PEB A, polytetrafluoroethylene ("PTFE"), polyetheretherketone ("PEEK"), other polymers, thermoplastic polyurethane ("TPU"), polyethylene with pebble stone surface, silicone oil stainless steel, Nitinol, other metals, or combinations thereof. In at least one embodiment, the central lumen lining may include a plurality of PEBA materials having different durometers.

In other embodiments, the guide catheter 105 may also have an outer layer. In some embodiments, the outer layer may be made of or include a single material or may be made of or include different materials to impart different handling characteristics to the guide catheter 105. For example, the outer layer may be made of or include softer materials to promote flexibility of the guide catheter 105. In other examples, the outer layer may be made of or include stiffer materials to promote pushability and/or torqueability of the guide catheter 105. In yet other examples, the outer layer may include lubricious materials to reduce friction between the guide catheter 105 and the body lumen of the patient. The outer layer may include PEBA, polytetrafluoroethylene ("PTFE"), polyetheretherketone ("PEEK"), other polymers, thermoplastic polyurethane ("TPU"), polyethylene with pebble stone surface, silicone oil stainless steel, Nitinol, other metals, or combinations thereof. In at least one embodiment, the outer layer may include a plurality of PEBA materials having different durometers.

In some embodiments, the outer layer of guide catheter 105 may also include a radiopaque marker to improve visualization of guide catheter 105 during a medical procedure. For example, the outer layer may include a barium sulfate (BaSO4), gold, platinum, platinum iridium, iodine, other radiopaque materials, or combinations thereof on a distal portion of guide catheter 105. In at least one embodiment, one or more additional radiopaque markers may be longitudinally located at one or more intermediate locations along the length of guide catheter 105.

The curves of guide catheter 105 may be formed by any suitable means. In some embodiments, one or more of the curves are preset so that the curve is formed by shape memory. For example, guide catheter 105 may be comprised of a flexible polymer material in which a curve is preset by heating. When guide catheter 105 is loaded on a guidewire, dilator, obturator or introductory device, the flexibility of guide catheter 105 can allow it to follow the shape or path of the introductory device for proper positioning within the body. When the introductory device is pulled back and/or removed, guide catheter 105 can then resume the shape memory configuration which was preset into the catheter.

Alternatively, the curves may be formed or enhanced with the use of one or more steering mechanisms. In some embodiments, the steering mechanism comprises at least one control wire or pull wire attached to one of the guide catheter 105, wherein actuation of the steering mechanism applies tension to the at least one pull wire whereby the curve is formed. The pull wires can extend through the central lumen or through individual lumens in the wall of guide catheter 105. It may be appreciated that more than one pull wire may extend through any given lumen. The presence of each pull wire allows curvature of guide catheter 105 in the direction of the pull wire. For example, when pulling or applying tension to a pull wire extending along one side of the catheter, the catheter will bend, arc or form a curvature toward that side. To then straighten the catheter, the tension may be relieved for recoiling effects or tension may be applied to a pull wire extending along the opposite side of the catheter. Therefore, pull wires are often symmetrically placed along the sides of the catheter.

Thus, in some embodiments at least two pull wires are attached in diametrically opposed locations wherein applying tension to one of the pull wires curves the catheter in one direction and applying tension to the pull wire attached in the diametrically opposed location curves the catheter in another direction opposite to the one direction. The diametrically opposed pull wires may be considered a set. Any number of sets may be present in a catheter to provide unlimited directions of curvature. In some embodiments, the steering mechanism can comprise at least four pull wires wherein two of the at least four pull wires are attached to the guide catheter in diametrically opposed locations and another two of the at least four pull wires are attached to the guide catheter in diametrically opposed locations. In other words, the catheter may include two sets of pull wires, each set functioning in an opposing manner as described. When the two sets of pull wires are positioned so that each pull wire is 90 degrees apart, the catheter may be curved so that the distal end is directed from side to side and up and down. In other embodiments, the steering mechanism comprises at least three pull wires, each pull wire symmetrically positioned approximately 120 degrees apart. When tension is applied to any of the pull wires individually, the catheter is curved in the direction of the pull wire under tension. When tension is applied to two pull wires simultaneously, the catheter is curved in a direction between the pull wires under tension. Additional directions may also be achieved by various levels of tension on the pull wires. It may be appreciated that any number, combination and arrangement of pull wires may be used to direct the catheters in any desired direction.

In some embodiments, a portion of one of guide catheter 105 can comprise one or more articulating members. In this case, the at least one pull wire is attached to one of the articulating members so that the curve is formed by at least some of the articulating members. Each pull wire is attached to the catheter at a location chosen to result in a particular desired curvature of the catheter when tension is applied to the pull wire. For example, if a pull wire is attached to the most distal articulating member in the series, applying tension to the pull wire will compress the articulating members proximal to the attachment point along the path of the pull wire. This results in a curvature forming in the direction of the pull wire proximal to the attachment point. It may be appreciated that the pull wires may be attached to any location along the catheter and is not limited to attachment to articulating members. Typically, the articulating members comprise inter-fitting domed rings but may have any suitable shape.

It may also be appreciated that curves in guide catheter 105 may be formed by any combination of mechanisms. For example, a portion of guide catheter could form a curve by shape memory while a different portion of guide catheter could form a curve by actuation of a steering mechanism.

The steering mechanisms may be actuated by manipulation of actuators located on handle 110. The handle 110 can be connected with the proximal end of the guide catheter 105 and remains outside of the body. One or more actuators or controls 120 can be provided on handle 110 and may have any suitable form, including buttons, levers, knobs, switches, toggles, dials, or thumbwheels, to name a few. When pull wires are used, each actuator may apply tension to an individual pull wire or to a set of pull wires. The handle may also include one or more locking mechanisms configured to interface with, and selectively lock into place, one or more of the controls 120.

In at least one embodiment, the handle 110 includes at least one control 120 for actuating and/or adjusting one or more components of a cutting mechanism 130. As shown in FIG. 1, the cutting mechanism 130 is configured to extend beyond the distal end 115 of the guide catheter 105. In at least one embodiment, the cutting mechanism 130 is routable through the guide catheter 105 and retractable into the guide catheter 105. The at least one control 120 may control the cutting mechanism's 130 extension from, and retraction into, the guide catheter 105. Additionally or alternatively, the at least one control 120 may be configured to provide selective actuation of the cutting mechanism 130. The at least one control 120 may be operatively connected to one or more additional elements of the cutting mechanism 130. The cutting mechanism 130 is shown here in generic form as a dashed line, and therefore represents any of the cutting mechanism 130 embodiments described herein.

Figure 2:
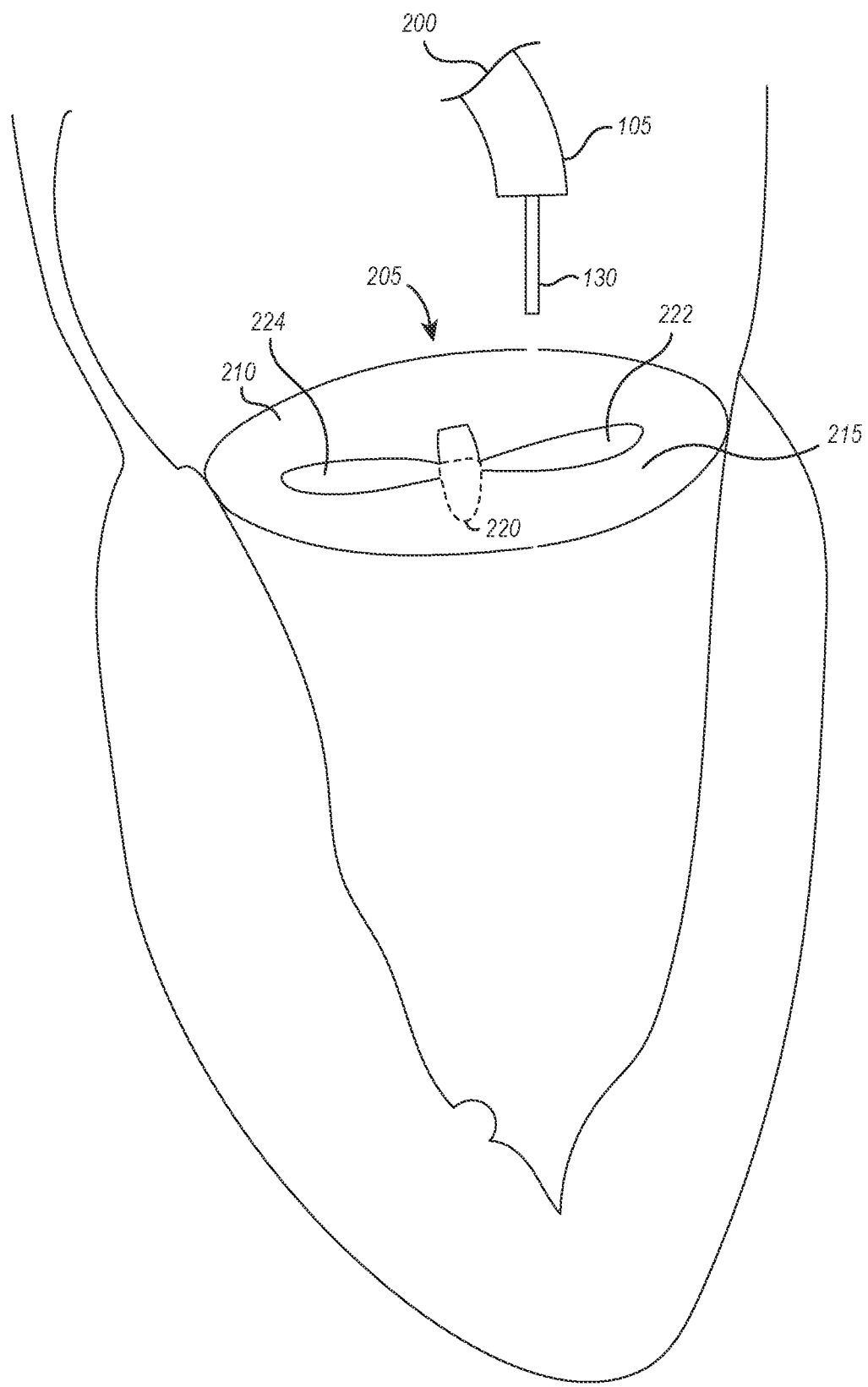
FIG. 2 is a schematic representation of a human heart with an interventional implant affixed between the anterior and posterior leaflets of the mitral valve and a guiding catheter extending from a transseptal puncture and positioned above the mitral valve.

FIG. 2 is a schematic representation of a human heart with an interventional implant affixed between the anterior and posterior leaflets of the mitral valve. The mitral valve comprises a posterior mitral leaflet 210 and an anterior mitral leaflet 215. FIG. 2 also shows an interventional implant (e.g., MitraClip®) 220, which has previously been affixed to the leaflets in an effort to reduce regurgitation by approximating the adjacent leaflets 210 and 215. As shown, the affixation of implant 220 to the leaflets creates a first orifice 222 and a second orifice 224 located on opposing sides of implant 220 and between the anterior mitral leaflet 215 and the posterior mitral leaflet 210. And, as discussed above, if further treatment is required in the form of the installation of an artificial, replacement mitral valve, the prior clip implant 220 must be detached from one or both of the leaflets before the replacement valve can be implanted.

In use, the leaflet cutting system 100 can be inserted into, and navigated through a patient's vasculature in a conventional manner to arrive in the patient's heart. As also illustrated in FIG. 2, a distal end portion of the leaflet cutting system 100 can be inserted through the interatrial septum 200 of the heart and positioned above the mitral valve in preparation for a leaflet cutting procedure. In at least one embodiment, the distal end 115 of the guide catheter 105 can include one or more radiopaque or echogenic markers to aid in accurate positioning. One skilled in the art will appreciate that the positioning of the distal end portion of the guide catheter 105 of the leaflet cutting system 100 in FIG. 2 is merely exemplary, and the present disclosure is not limited to the specific positioning shown.

Referring next to FIGS. 3A-3D, which illustrate a first embodiment of a leaflet cutting system 100. System 100 includes components corresponding to those described above in connection with FIG. 1, which are designated by the same reference numerals throughout. As shown in FIGS. 3A-3D, system 100 also includes a cutting mechanism 130a positioned within, and routed through, the guide catheter 105. As shown, the cutting mechanism 130a may comprise an elongate inner catheter or hypotube 300, extending from a proximal end (not shown in FIG. 3) to a distal end 302 of the leaflet cutting system 100. The proximal end of the cutting mechanism 130a can be operatively coupled to the handle 110, and handle 110 provided with controls adapted to manipulate the cutting catheter 130a, including advancing, retracting and/or rotating the cutting mechanism 130a relative to the guide catheter 105.

Figure 3A:
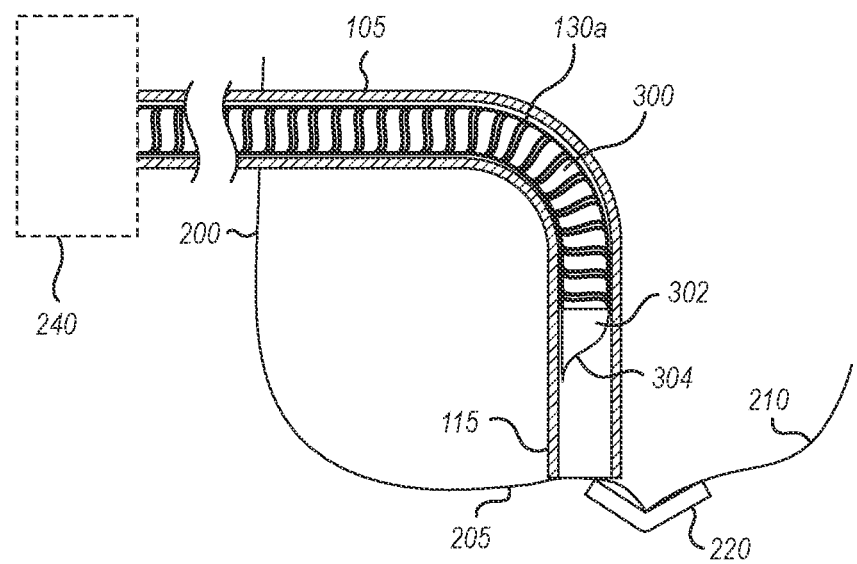
FIGS. 3A-3D illustrate an embodiment of a cutting mechanism according to the present disclosure shown in use in association with a cardiac valve.

As shown in FIG. 3A, cutting mechanism 130a is positioned within the interior of guide catheter 105 during advancement and positioning of the system 100 above the mitral valve 205. As discussed below, once the distal end 115 of guide catheter 105 is properly positioned above the mitral valve 205 and in proper alignment with interventional implant 220, the handle 110 can be manipulated to cause cutting mechanism 130a to advance relative to guide catheter 105 and to pass through the tissue of one of the leaflets 210, 215, thereby cutting the affected leaflet and separating the interventional implant 220 from the affected leaflet.

In this embodiment, the cutting mechanism 130a can have at its distal end 302, a sharped end 304 that terminates in a point. The sharpened end 304 may have a circular or oval cross-sectional shape. The sharpened end 304 can also have tapered, sharpened edges or blades adjacent to and extending from the point, which are adapted to slide through the leaflet tissue located between the first and second orifices 222, 224 and adjacent the interventional implant 220. In this and other embodiments described herein, the components of cutting mechanism 130a may be formed from the same or different materials, including but not limited to stainless steel or other metals, Elgiloy®, nitinol, titanium, tantalum, metal alloys or polymers.

Figure 3B:
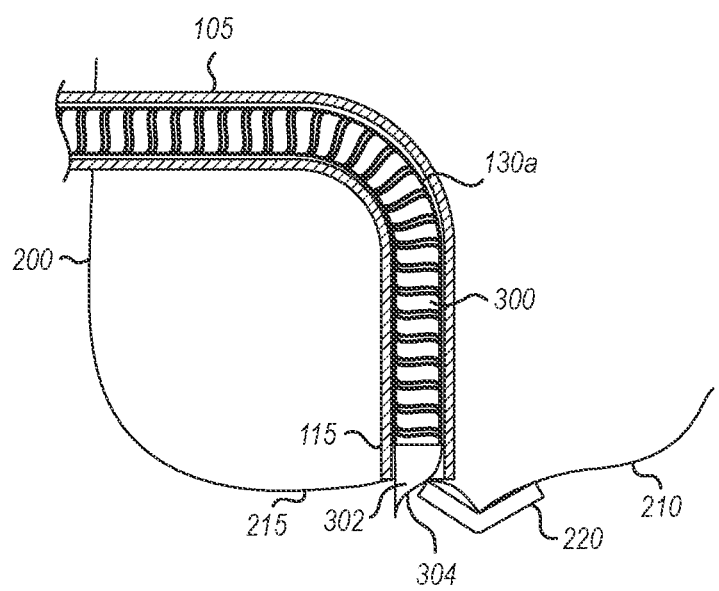
Figure 3C:
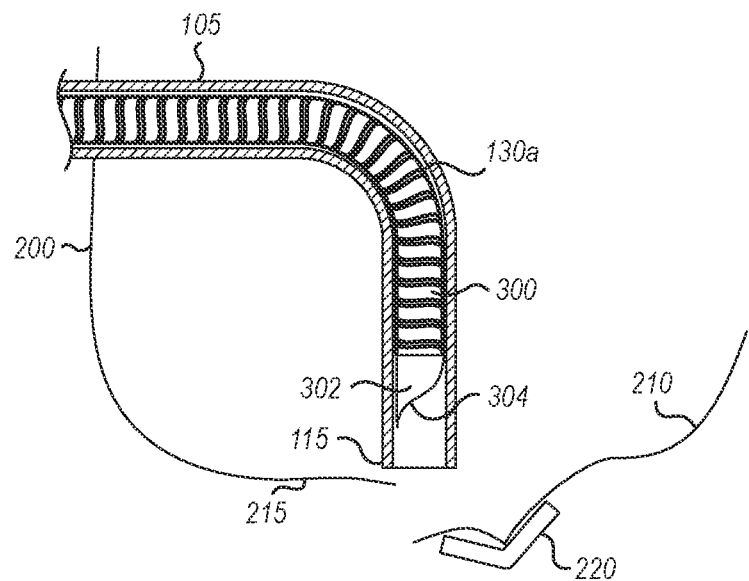
Figure 3D:
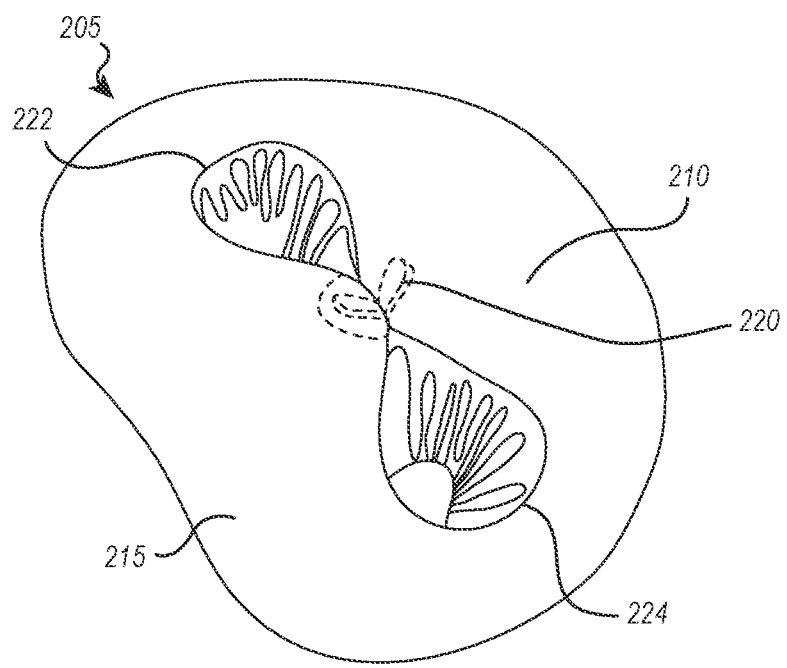

FIG. 3B also shows how the hypotube 300 may be advanced to cause the sharpened end 304 to extend from the distal end 115 of the guide catheter 105 and cut a portion of the anterior mitral leaflet 215. The point of sharpened end 304 helps anchor and stabilize the leaflet tissue as the sharpened, cutting edges of the cutting mechanism 130a are advanced through and cut the leaflet tissue. The circular or oval cross section of sharpened end 304 of the cutting mechanism 130a cause the sharpened end to cut through the leaflet tissue in an arc around the interventional implant and extending from the first orifice 222 to the second orifice 224, as schematically illustrated in FIG. 3D. After the sharpened end 304 of cutting mechanism 130a advances and cuts through the tissue of the anterior mitral leaflet 215, the interventional implant 220 may remain attached to the posterior mitral leaflet 210, as shown in FIG. 3C, thereby reducing the risk that the interventional implant 220 will interfere with functioning of the left ventricular outflow tract. Additionally or alternatively, the posterior mitral leaflet 210 may also be cut in a similar manner with little or acceptable risk of left ventricular outflow tract interference. In at least one embodiment, the interventional implant 220 is removed from the patient.

FIG. 3D is a top perspective view of a mitral valve showing the cut portion of the anterior mitral leaflet 215. As shown, the sharpened end 304 may cut an arc in the leaflet 210 around the interventional implant 220. The hypotube 300 may be sized depending on the number of interventional implants 220 that are located within the cardiac valve. Additionally or alternatively, a single hypotube 300 may be used to cut multiple interventional implants 220 within a cardiac valve.

In this and other embodiments described herein, inner catheter or hypotube 300 should preferably have sufficient flexibility as to be able to conform to bends formed by guide catheter 105. Additional flexibility to accommodate bending may be provided in certain regions of hypotube 300 by a series of laser cuts formed in the outer wall of hypotube 300. In addition, hypotube 300 should also provide sufficient compressive strength to permit forces to be transmitted through hypotube 300, from the proximal end to the distal end, sufficient to cause the sharpened end 304 of hypotube 300 to cut through the leaflet tissue.

In an alternate embodiment, an indeflator 240 can be attached to the guide catheter 105 at or near its proximal end. The indeflator 240 can be configured to create a vacuum transmitted through the lumen of the guide catheter 105. When the distal end of the guide catheter is positioned against the leaflet, a negative pressure can be applied to the leaflet tissue, thereby stabilizing nearby leaflet tissue located adjacent the interventional implant 220. While leaflet tissue adjacent to the clip implant 220 is held in place by the negative vacuum pressure applied through the distal end of the guide catheter, the hypotube 300 can be advanced relative to the guide catheter 105, thereby causing the sharpened end 304 to pass through and cut the leaflet tissue surrounding the clip implant 220. In this alternate embodiment, a distal end portion of the guide catheter 105 may comprise various cross-sectional shapes including a U-shape. For example, the distal end 115 of the guide catheter 105 can comprise a flexible U-shape that may collapse when positioned within a delivery sheath and then expand when the guide catheter is advanced to extend beyond the distal end of the delivery sheath.

In another alternate embodiment, in addition to the sharpened edges located at the distal end of the cutting mechanism 130a used for mechanical cutting, the cutting mechanism 130a could also include an electrical conductor (not shown) that extends along its entire length, which conductor is electrically coupled at a distal end to the sharpened cutting end 304 and which is also electrically coupled at a proximal end to a source for selectively applying electrosurgical energy, such as an electrosurgical generator. In that case, the cutting of leaflet tissue could be achieved by mechanical cutting, by the application of electrosurgical energy, or a combination of both.

Figure 4A:
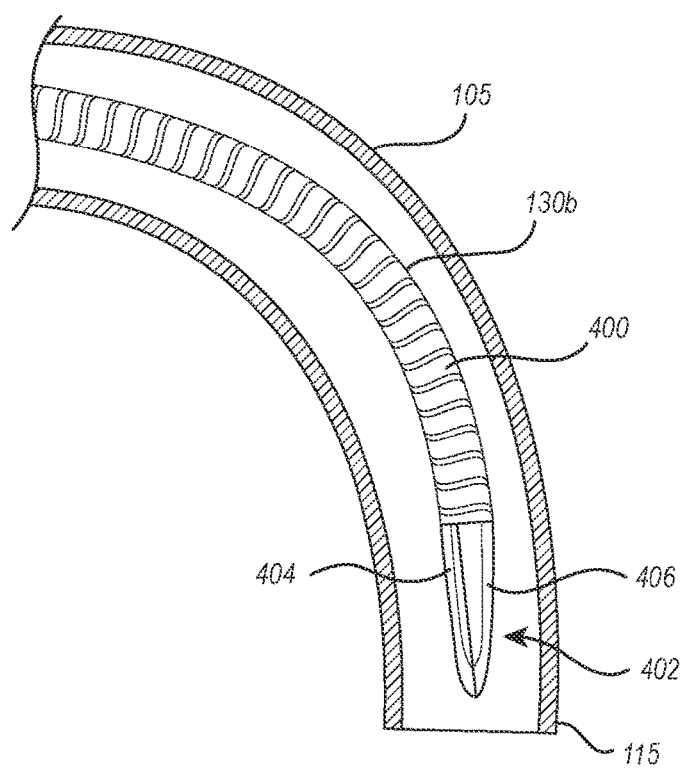
Figure 4B:
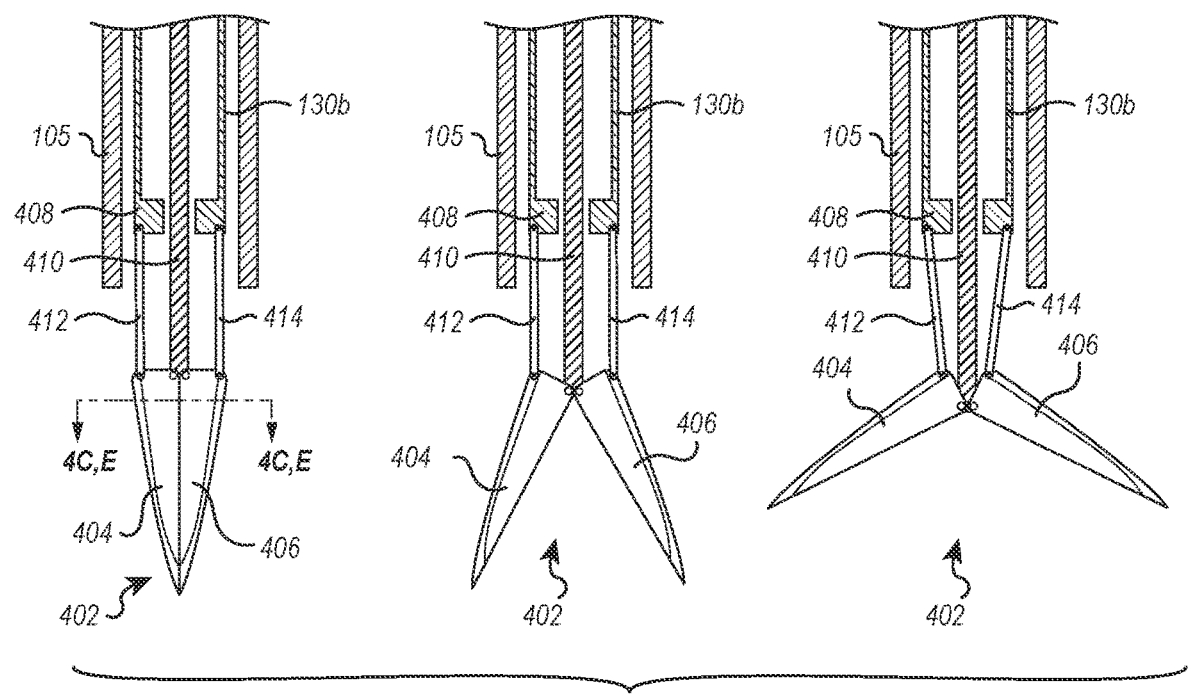

Reference is next made to FIGS. 4A-4F, which illustrate a second embodiment of a cutting mechanism 130b. This embodiment also includes components corresponding to those described above in connection with FIG. 1, which are designated by the same reference numerals throughout. FIG. 4A is a side sectional view of the cutting mechanism 130b shown within the distal end 115 of the guide catheter 105. As shown, the cutting mechanism 130b may comprise an inner catheter or hypotube 400 having a sharpened, cutting end 402, which terminates at its distal end in a sharpened point. This embodiment, the sharpened cutting end 402 can include two blades 404 and 406 joined at a pivot point. The two blades 404 and 406 may each comprise a cutting edge disposed on an outer edge of each blade as illustrated in FIG. 4B. The hypotube 400 may be configured to be selectively extended from the distal end 115 of the guide catheter 105, thereby allowing the two blades 404 and 406 to engage with a portion of leaflet tissue.

In this embodiment, the blades 404 and 406 can be connected to the hypotube 400 in such a way that, when actuated, the blades pivot outwardly away from one another in an arcuate path in a "reverse-scissor" fashion. In the illustrated embodiment, this can be accomplished as follows. A tip ring 408 can be integrally attached to the distal end of the hypotube. Tip ring 408 can include a center lumen that allows an actuating rod 410 to extend therethrough as shown in FIG. 4B. The actuating rod 410 can be pivotally connected at its distal end to a center portion of the proximal ends of each of blades 404 and 406 as shown. Links 412 and 414 can also be provided, which connect a distal end of tip ring 408 to an outer portion of the proximal ends of each of blades 404 and 406. While not explicitly shown in FIG. 4, hypotube 400 and actuating rod 410 can run the entire length of delivery system 102 and can be operatively coupled at their proximal ends to handle 110, and handle 110 can be provided with suitable controls to allow manipulation of hypotube 400 and actuating rod 410 relative to one another to cause blades 404 and 406 to open and close relative to one another. It will be appreciated that advancing actuating rod 410 relative to hypotube 400 will cause blades 404 and 406 to open in an arcuate path away from one another, and that withdrawing actuating rod 410 relative to hypotube 400 will cause blades 404 and 406 to close and move toward one another. Alternatively, actuating rod 410 could be held stationary and hypotube 400 moved relative to actuating rod 410 to open and close blades 404 and 406. Other structures and mechanisms known to those skilled in the art could be adapted and used for opening and closing blades 404 and 406 and are intended to be encompassed within the scope of the invention.

The cross-sectional shape of blades 404 and 406 can be selected to influence that shape of the path they travel as they cut through leaflet tissue. For example, in one embodiment illustrated in FIG. 4C, blades 404 and 406 can have a relatively straight or flat cross-sectional shape, which will cause the blades to cut through the leaflet tissue in a relatively straight path. Referring to FIG. 4D, the cut through the leaflet tissue can be made in multiple segments. For example, with blades 404 and 406 closed, the sharpened end 402 can be inserted at a first insertion point 416a into and through leaflet 210. The sharpened point and sharpened edges of sharpened end 402 assist with the ease of insertion and also help stabilize the tissue adjacent to the interventional implant 220. Once inserted through the tissue, blades 404 and 406 can be actuated by means of handle 110, acting through hypotube 400 and actuating rod 410, to cause the blades to open, thereby cutting through the leaflet tissue located to either side of insertion point 416a. The cutting mechanism can then be withdrawn in a proximal direction, repositioned, re-advanced in a distal direction through the tissue at a second insertion point 418a, re-actuated, and then at a third insertion point 418c, and so and so forth until the process completed to create a continuous cut through the affected leaflet tissue around the interventional implant 220 and extending from the first orifice 222 to the second orifice 224. Alternatively, the opening and closing of blades 404 and 406 can simply be reciprocated as the guide catheter 105 is used to drag the cutting blades through the leaflet tissue.

In an alternate embodiment, as illustrated in FIGS. 4E-4F, the two blades 404 and 406 can be shaped such that they cut the portion of leaflet tissue in an arcuate path. As best shown in FIG. 4E, blades 404 and 406 can also be made to have a cross-sectional shape that is circular or oval in shape. As with the above, the pointed end of sharpened end 402 is advanced through an entry point 416a into the leaflet tissue. However, when actuated, the shape of blades 404 and 406 cause them to travel in an actuate path through the leaflet tissue, as illustrated in FIG. 4F.

The cut portion in FIG. 4F is shown on the anterior leaflet 215, however, the present invention is not limited to the positioning of shape or cut. In at least one embodiment, the posterior mitral leaflet 210 can also be cut. Additionally or alternatively, the interventional implant 220 may be removed from the patient.

Reference is next made to FIGS. 5A-5J, which illustrate yet another embodiment of the cutting mechanism. In this embodiment, cutting mechanism 130c may comprise a first and a second delivery catheter 500 and 502, each comprising a proximal end and a distal end. The first delivery catheter 500 can include at its distal end a pair of grasping arms 504 and 506, which arms can be rotatably coupled to the distal end of delivery catheter 500 by a rotatable hub 508. Similarly, second delivery catheter 502 can include at its distal end a pair of grasping arms 510 and 512, which arms can be rotatably coupled to the distal end of delivery catheter 502 by a rotatable hub 514. One or more of grasping arms 504, 506, 510 and/or 512 may include one or more teeth to prevent slippage when the arms are engaged with leaflet tissue.

A cutting wire 516 may extend from the hub 508 of the first delivery catheter 500 to the 514 of the second delivery catheter 502. The cutting wire 516 may be configured to selectively provide electrosurgical energy to a secured portion of leaflet tissue, thereby cutting a portion of leaflet tissue when rotated around hubs 508 and 514. Additionally or alternatively, an adjustment in the tension of cutting wire 516 may cause the wire 516 to engage with and cut the secured leaflet tissue.

Figure 5A:
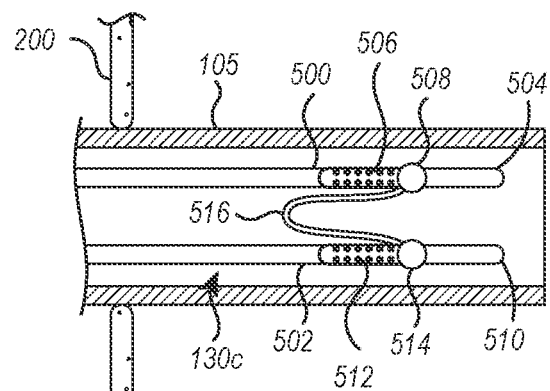
Figure 5B:
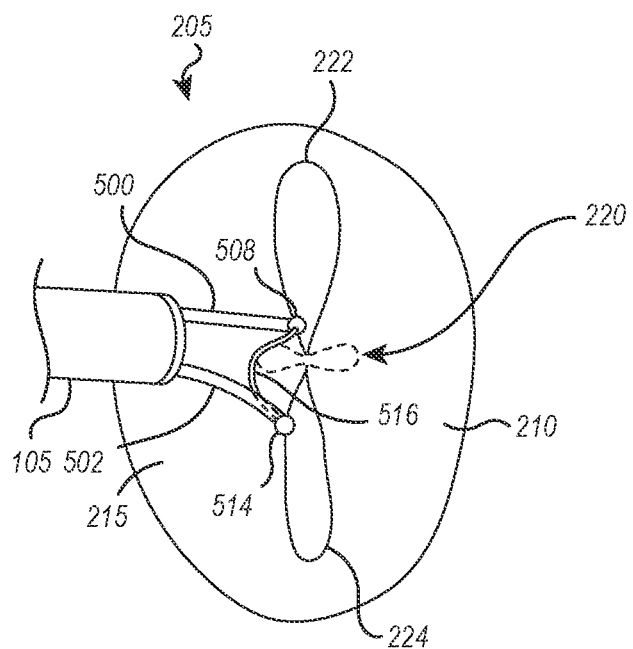
Figure 5G:
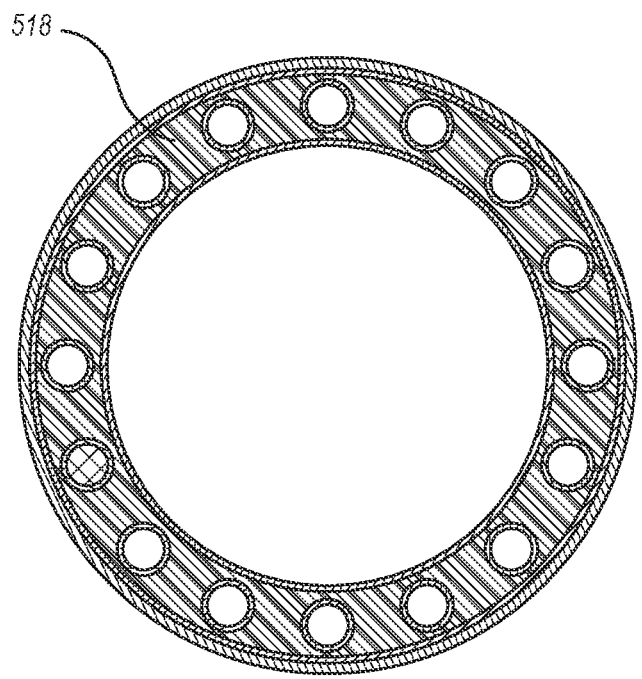
Figure 5H:
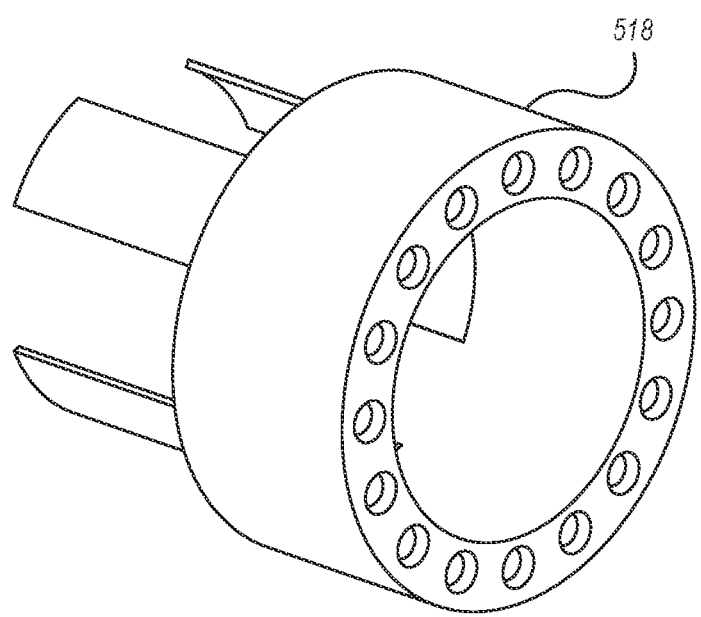

As shown in FIG. 5B, which is a top perspective view of a mitral valve, the first and second delivery catheters 500 and 502 may be configured to extend from the distal end 115 of the guide catheter 105. The interventional implant 220 creates a first orifice 222 and a second orifice 224 between the anterior mitral leaflet 215 and the posterior mitral leaflet 210 by approximating the adjacent leaflets 210 and 215. The first delivery catheter 500 may extend toward the first orifice 222 and thereby extend the first grasping arm 504 (not shown in FIG. 4B) of the first delivery catheter 500 into the first orifice 222 of the mitral valve. Similarly, the second delivery catheter 502 may extend toward the second orifice 224 and thereby extend the first grasping arm 510 (not shown in FIG. 4B) of the second delivery catheter 502 into the second orifice 224 of the mitral valve. The first grasping arms 504 and 510 may be configured to engage with leaflet tissue on the ventricular side of the mitral valve.

FIGS. 5C and 5D are a detailed side views of the distal end of delivery catheter pair 500 and 502 at various stages of positioning and deployment to attach and hold onto a portion of the tissue of one of the leaflets 205, with one delivery catheter 500 attaching to the leaflet 210 to one side of the interventional implant 220 and the other delivery catheter 502 attaching to the same leaflet 210 on the other side of the interventional implant 220. Once the guide catheter 105 is properly positioned above and aligned with the interventional implant 220, delivery catheters 500 and 502 are advanced relative to the guide catheter 105 to extend beyond the distal end 115 of guide catheter 105. The distal ends of delivery catheters 500 and 502 are advanced until grasping arms 504 and 510 pass through orifices 222 and 224 of the mitral valve on opposites side of the interventional implant 220, as shown in FIG. 5C. Guide catheter 105 can then be manipulated to reposition grasping arms 504 and 510 into direct contact with the edges of orifices 222 and 224, as also shown in FIG. 5C. Once that is done, grasping arms 504 and 506 of delivery catheter 500 can be rotated toward one another to clamp down on the leaflet tissue adjacent the first orifice 222 (and located to one side of the interventional device 220), and grasping arms 510 and 512 of delivery catheter 502 can similarly be rotated toward one another to clamp down on either side of the leaflet tissue adjacent the second orifice 224 (and located to the other side of the interventional device 220), as shown in FIG. 5D. Once the leaflet tissue is secured between grasping arms 504 and 506 and between grasping arms 510 and 512, then cutting wire 516 can be rotated to cut through the leaflet tissue and separate the interventional implant 220 from the affected leaflet, as illustrated in FIGS. 5E and 5F.

Figure 5I:
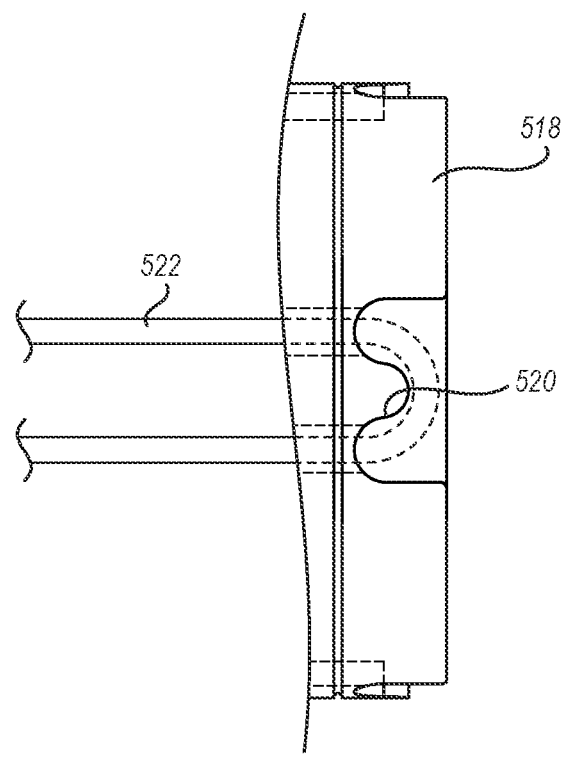
Figure 5J:
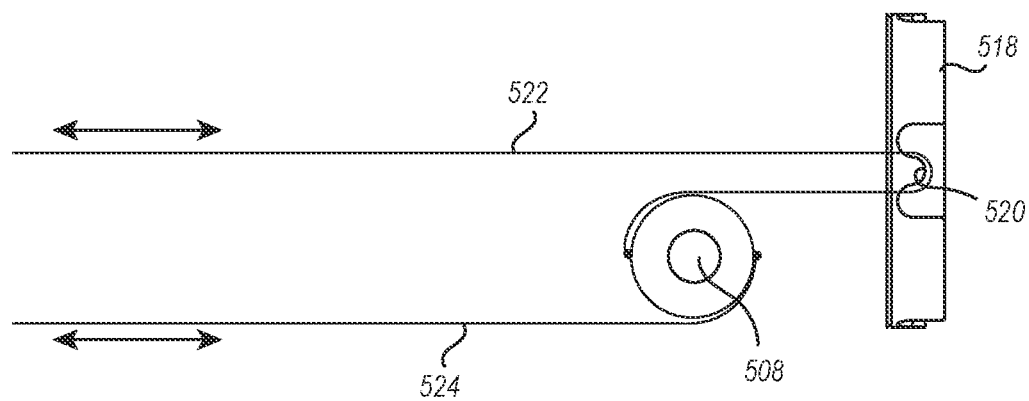

FIGS. 5G-5J illustrate one example of a mechanism of actuating the various components of cutting mechanism 130c described above. However, additional structures and mechanisms known to those skilled in the art could be adapted and used for controlling the selective, relative rotation of grasping arms 504, 506, 510 and 512, as well as that of cutting wire 516. In one embodiment, each of delivery catheters 500 and 502 can include at their respective distal ends a tip ring 518, having a plurality of lumens for accepting a plurality of control lines. Each control line, such as control line 522 shown in FIGS. 5H and 5I, can be coupled at the proximal end of the system 100 to a dedicated control located on handle 110. Separate control lines can be provided to separately and independently control selective movement of each of grasping arms 504, 506, 510 and 512, as well as movement of cutting wire 516. Certain control lines, such as control line 522, can extend the entire length of the system and pass around a saddle, such as saddle 520 formed in tip ring 518 between adjacent lumens, as shown in FIGS. 5I and 5J, so that the control line returns in a proximal direction for attachment to one of the rotatable hubs, such as rotatable hub 508, as shown in FIG. 5J. As further shown in FIG. 5J, control line 522 can be mechanically coupled to the periphery on one side of hub 508, and a second control line 524 can be mechanically coupled to the periphery of the other side of hub 508. As will be readily understood, selectively pulling on control line 522 will cause hub 508 to rotate in clockwise direction, and selectively pulling on control line 524 will cause hub 508 to rotate in counter-clockwise direction. By providing multi-part hubs and separate control lines for each component, relative movement and control of grasping arms 500 and 502, grasping arms 510 and 512, and cutting wire 516 can be effectuated from the proximal end of system 100 by means of one or more controls 120 provided on handle 110.

FIGS. 5C-5F illustrate how the grasping arms 504, 506, 510 and 512 are configured to secure a portion of the anterior mitral leaflet 215 therebetween and show the cutting wire 516 as cutting a portion of the anterior mitral leaflet 215. However, in at least one embodiment the posterior mitral leaflet 210 can be cut. The interventional implant 220 may additionally or alternatively be removed. As shown in FIGS. 5E and 5F, the cutting wire 516 may be rotated through the secured portion of the anterior mitral leaflet 215, thereby cutting the portion of leaflet tissue.

In at least one embodiment, the space between the first and second delivery catheters 500 and 502 may be adjusted based on number of interventional implants 220 within the mitral valve. Additionally or alternatively, the cutting mechanism 130c may be configured to retract into the distal end 115 of the guide catheter 105 after the portion of leaflet tissue is cut. One skilled in the art will appreciate that the positioning shown in FIGS. 5C-5F is merely exemplary and the present invention is not limited to the positioning shown.

Figure 6A:
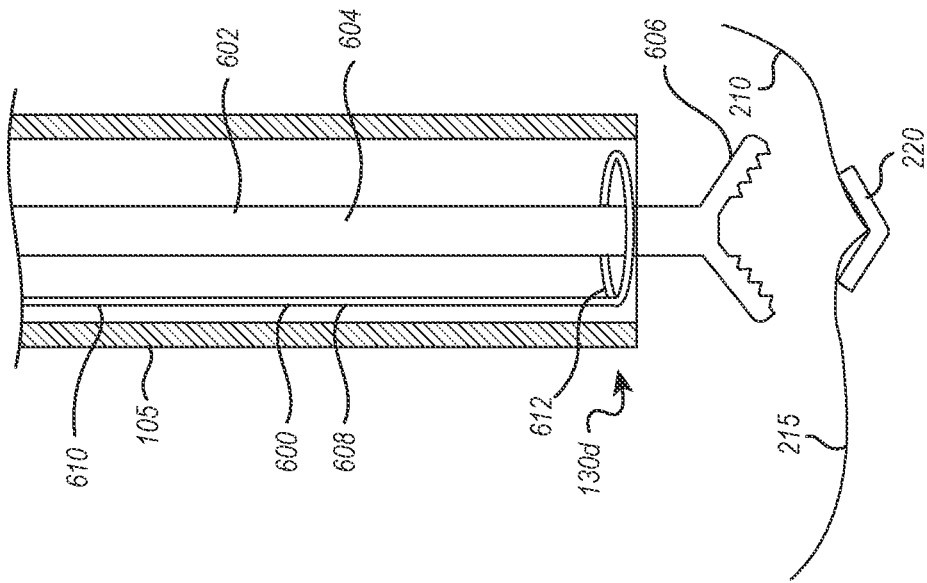
FIGS. 6A-6F illustrate an alternative embodiment of a cutting mechanism according to the present disclosure shown in use in association with a cardiac valve.
Figure 6B:
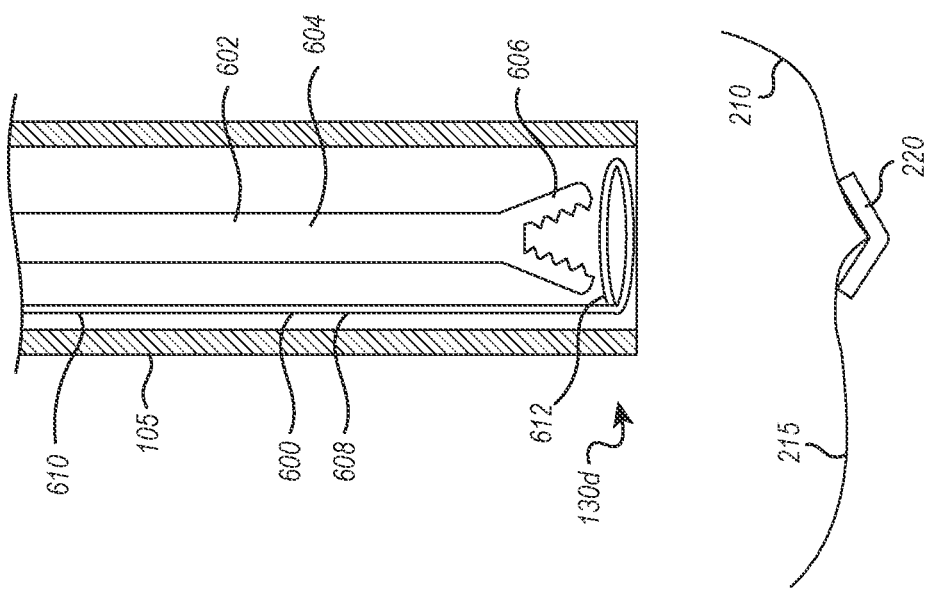

FIGS. 6A-6F are side sectional views and illustrate yet another alternative exemplary embodiment of a cutting mechanism shown in use in association with a cardiac valve, specifically a mitral valve. In this embodiment, the cutting mechanism 130d can include a clip grasping structure 602 and a cutting wire 608. FIG. 6B shows the distal end 115 of the guide catheter 105 positioned above the interventional implant 220, which approximates the anterior mitral leaflet 215 and posterior mitral leaflet 210. The cutting wire 608 can include an elongated portion 610 that terminates in a distal lasso or loop portion 612. The cutting wire 608 may extend from the handle 110 to the distal end 115 of the guide catheter 105. Further, the cutting wire 608 may be configured to selectively provide electrosurgical energy through the distal loop portion 612 to tissue in contact with distal loop portion 612. While the cutting wire 608 is shown as a separate component in FIGS. 6A-6D, a cutting electrode could also be integrally formed on the distal end 115 of guide catheter 105 and/or on the interior wall surface of guide catheter 105 adjacent the distal end 115.

FIGS. 6A-6F also illustrate a clip grasping structure 602 comprising an elongated portion 604 and a distal clamping portion 606, which may be routed through the guide catheter 105. As shown in FIG. 6B, the distal clamping portion 606 is extendable distally past the distal end 115 of the guide catheter 105. The distal clamping portion 606 may extend through the distal loop portion 612 of the cutting wire 608 when extending distally past the distal end 115 of the guide catheter 105.

Figure 6C:
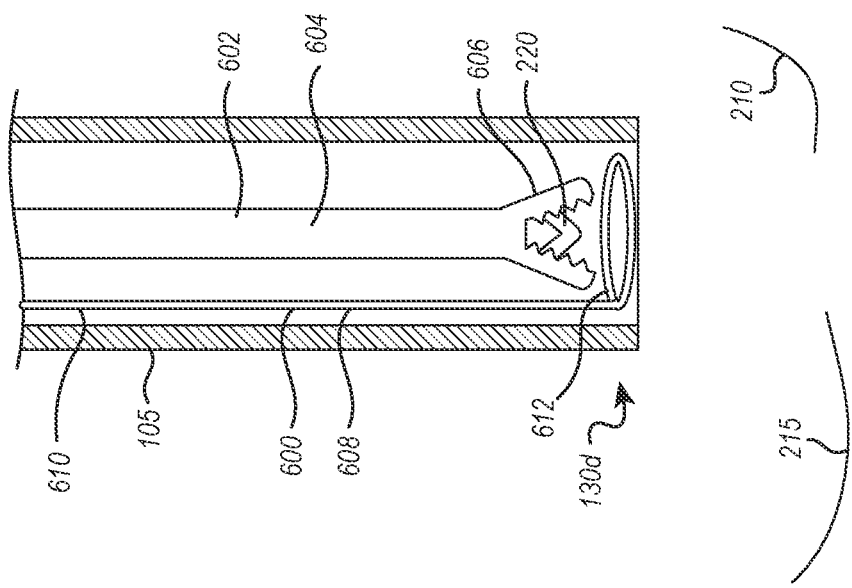
Figure 6D:
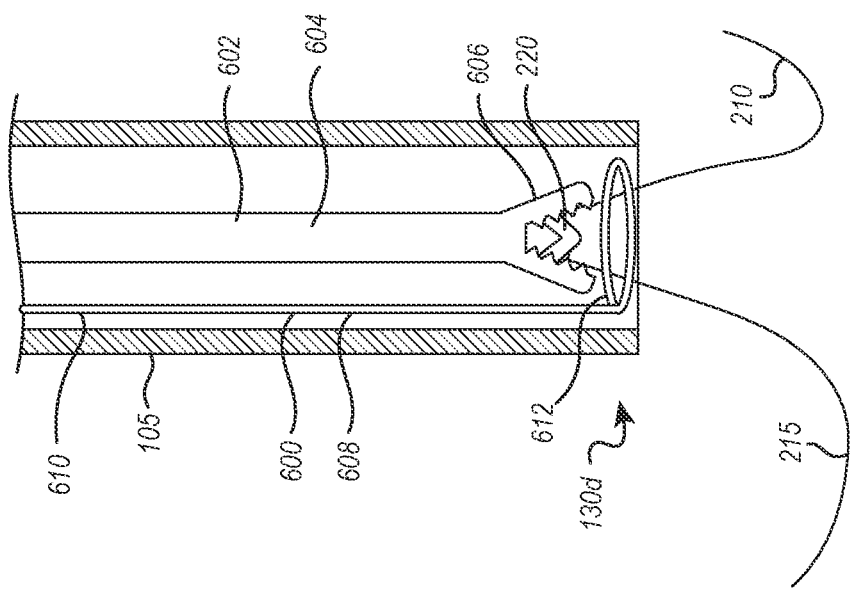

The distal clamping portion 606 may be configured to secure an interventional implant 220, as shown in FIG. 6C. The distal clamping portion 606 may also be retractable proximally into the distal end 115 of the guide catheter 105 with the secured interventional implant 220. In at least one embodiment, the distal clamping portion 606 extends through the distal loop portion 612 of the cutting wire 608 when retracting proximally into the distal end 115 of the guide catheter 105 with the secured interventional implant 220. As shown in FIG. 6D, the distal loop portion 612 of the cutting wire 608 may be configured to cut a portion of leaflet tissue when the distal clamping portion 606 of the clip grasping structure 602 retracts proximally into the distal end 115 of the guide catheter 105 with the secured interventional implant 220. The distal loop portion 612 of the cutting wire 608 may also be selectively constricted to engage with and cut the portion of leaflet tissue. In at least one embodiment, the cutting wire 608 is configured to detach the interventional implant 220 from surrounding leaflet tissue.

Figure 6E:
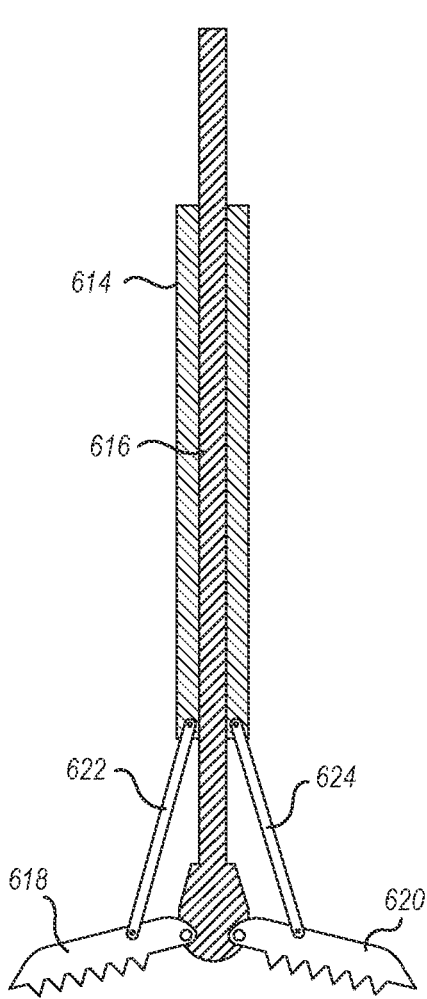
Figure 6F:
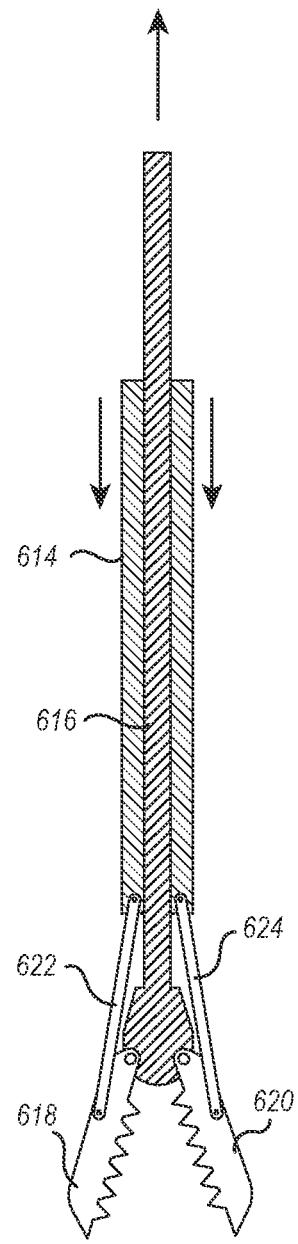

FIGS. 6E and 6F illustrate one example of a mechanism of actuating the distal clamping portion 606 of grasping structure 602. However, additional structures and mechanisms known to those skilled in the art could be adapted and used for selectively opening, closing and clamping distal clamping portion 606. In this embodiment, grasping mechanism 602 can include an elongate hypotube 614, an actuating rod 606, a pair of grasping arms 618 and 620, and a pair of links 622 and 624. A proximal end of each grasping arm 618 and 620 can be pivotally coupled to the distal end of actuating rod 616. Links 622 and 624 can each be pivotally connected at one end to the distal end of hypotube 614 and can be pivotally connected at the other end to an intermediate location on grasping arms 618 and 620, respectively. It should be further understood that hypotube 614 and actuating rod 616 can extend the entire length of the system and can be operatively coupled at their proximal ends to suitable controls 120 located on handle 110 to control movement of hypotube 614 and actuating rod 616 relative to one another and, thus, causing grasping arms to open and close. The tissue engaging surface of grasping arms 618 and 620 can also include one or more teeth to engage leaflet tissue adjacent the interventional implant and prevent slippage.

Figure 7A:
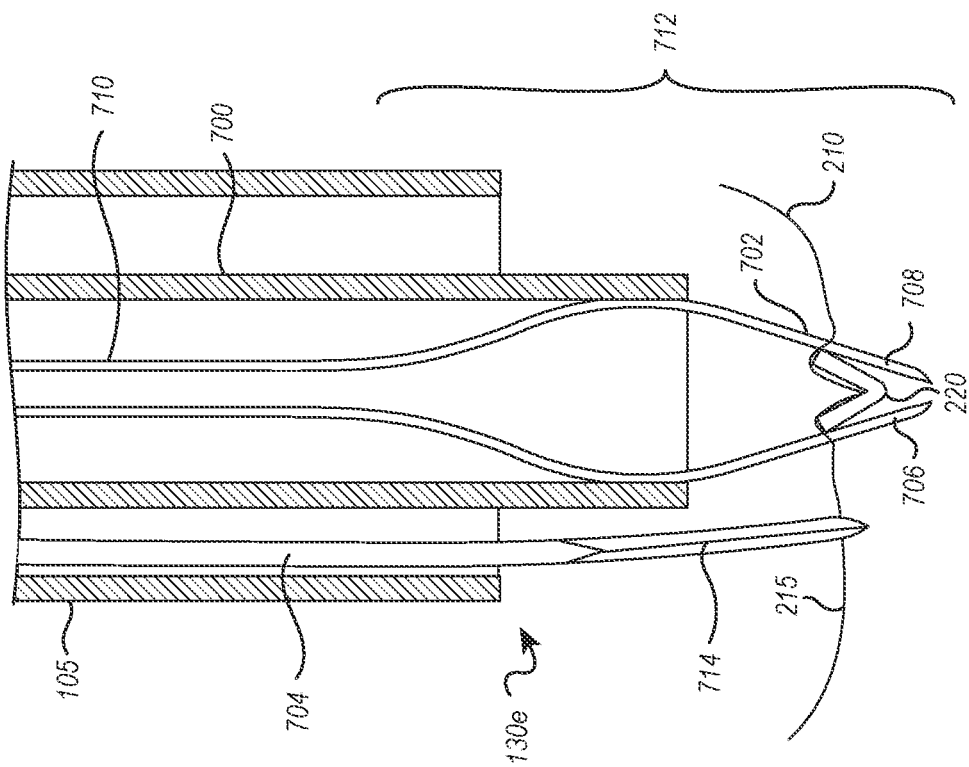
FIGS. 7A-7D illustrate alternative embodiment of a cutting mechanism according to the present disclosure shown in use in association with a cardiac valve.
Figure 7B:
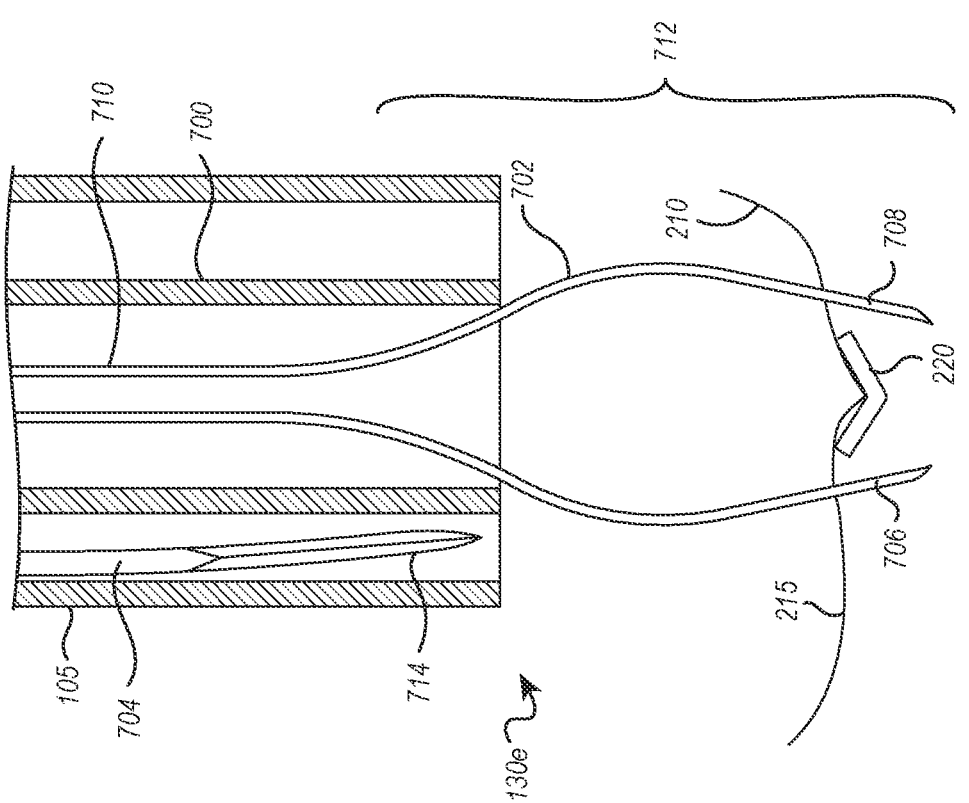
Figure 7C:
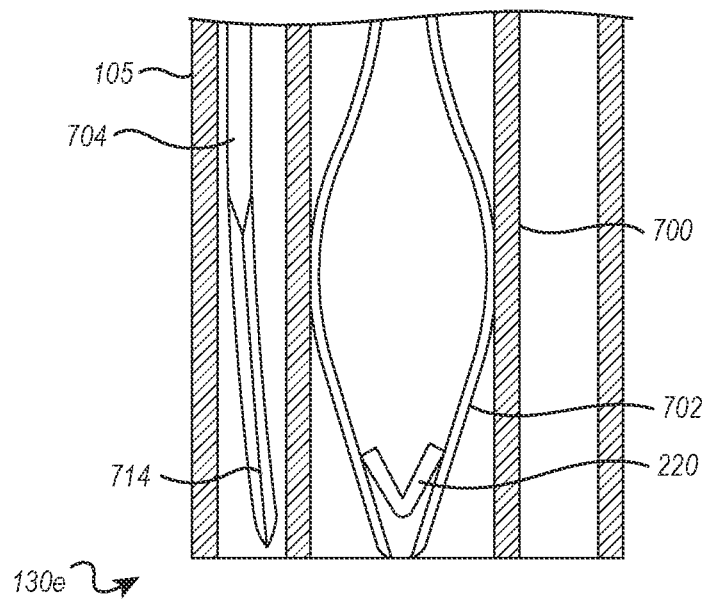

Reference is next made to FIGS. 7A-7D, which illustrate still yet another embodiment of a cutting mechanism for use in detaching an interventional device from one or more leaflets of a mitral valve. Cutting mechanism 130e can include an inner catheter or hypotube 700, a clip grasping structure 702 and an elongated cutter 704. As shown in Figures7A-7C, the distal end 115 of the guide catheter 105 may be positioned above the interventional implant 220. The elongated cutter 704 can be configured to be positioned within the lumen formed between the outer wall of the hypotube 700 and the inner wall of the guide catheter 105 and to selectively extend from the distal end 115 of the guide catheter 105. Cutter 704 can terminate at is distal end in a sharpened point adapted to pierce through leaflet tissue. Cutter 704 can also include one or more sharpened edges 714 (adapted to mechanically cut through the leaflet tissue) that extend along one or both sides of a distal section thereof. The elongated cutter 704 may rotate around the clip grasping structure in an arcuate path, thereby slicing through a portion of leaflet tissue. In at least one embodiment the elongated cutter 704 can be composed of a heat shaped material.

Figure 7D:
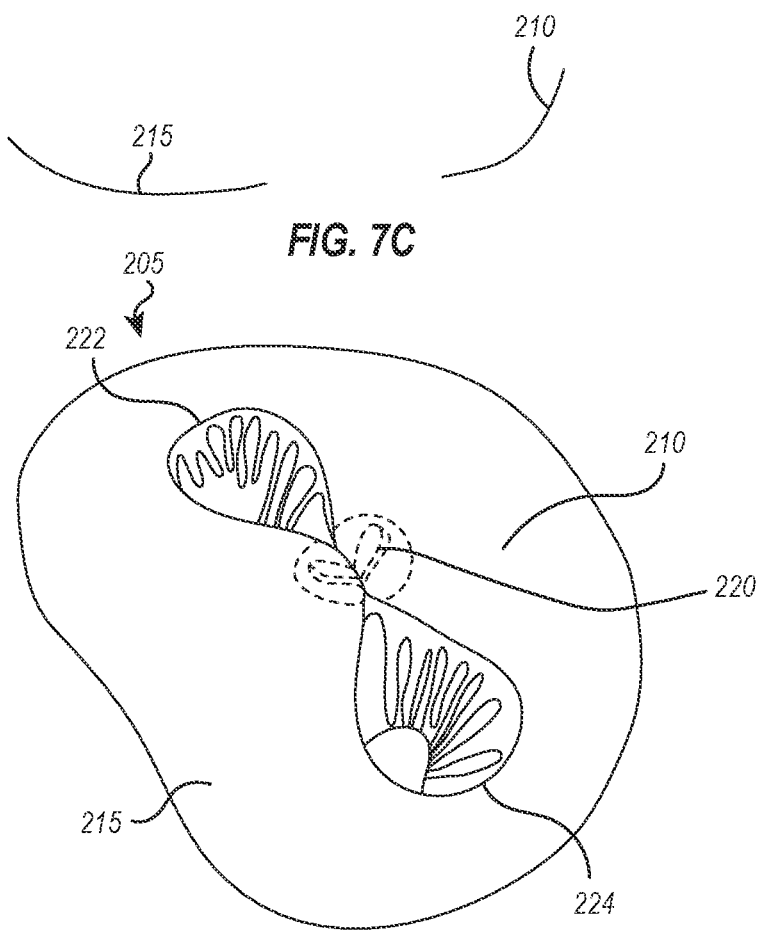

FIGS. 7A-7C further illustrate that hypotube 700 extends through the guide catheter 105 and can be positioned at the distal end 115 of the guide catheter 105. Clip grasping structure 702 may be routable through the hypotube 700 and positioned at a distal end of the hypotube 700. In at least one embodiment, the clip grasping structure 702 can comprise two flexible prongs 706 and 708, each of which preferably includes a sharpened tip adapted to pierce through the tissue of the mitral valve leaflets. The clip grasping structure 702 may comprise an elongated portion 710 and a distal clamping portion 712. As shown in FIGS. 7A and 7B, the distal clamping portion 712 of the clip grasping structure 702 may be extendable distally past the distal end 115 of the guide catheter 105 and the distal end of the hypotube 700. In at least one embodiment, the distal clamping portion 712 can be made of a semi-rigid, resilient metal. Once advanced beyond the distal end and freed from the constraints of hypotube 700, the distal clamping portion 712 can expand laterally as illustrated in FIG. 7A. Once in this configuration, the distal clamping portion 712 of the clip grasping structure 702 may be positioned around the interventional implant 220, and the assembly may then be advanced distally, causing the prongs 706 and 708 of distal clamping portion 712 to puncture through leaflet tissue located to either side of the interventional device 220. Then, as shown in FIG. 7B, hypotube can be advanced distally from the distal end 115 of the guide catheter 105 relative to the clip grasping structure 702, such that the hypotube 700 encloses a proximal portion of the distal clamping portion 712 of the clip grasping structure 702 within the hypotube 700, which also draws the prongs 706 and 708 closer together, thereby causing the distal clamping portion 712 of the clip grasping structure 702 to secure an interventional implant 220. The elongated cutter 704 may then be advanced relative to the guide catheter 105, hypotube 700 and clip grasping structure 702 to extend beyond the distal end 115 of the guide catheter 105 and engage with and cut the leaflet tissue. More specifically, the distal end of cutter 704 may be advanced through the first orifice 222 or the second orifice 224, and then the system can be rotated about its central axis, causing cutter 704 to travel in an arcuate path around the interventional device 220, slicing through the leaflet tissue located adjacent to the interventional device 220 as it travels from one orifice to the other. Of course, the cutter 704 could also be advanced through the leaflet tissue and then the system could be rotated back and forth until the entire cut from one orifice to the other orifice is complete. In addition, with this embodiment it is possible to cut through the tissue of both leaves of the mitral valve, thereby completely separating the interventional device 220 from the mitral valve. In that case, as shown in FIG. 7C, the hypotube 700 and distal clamping portion 712 of the clip grasping structure 702 can be retracted in a proximal direction relative to the guide catheter and into the distal end 115 of the guide catheter 105, thereby securing interventional implant 220. FIG. 7D shows the cut portion 610 of the anterior mitral leaflet 215, however the present invention is not limited to the positioning or shape of cut.

Figure 8A:
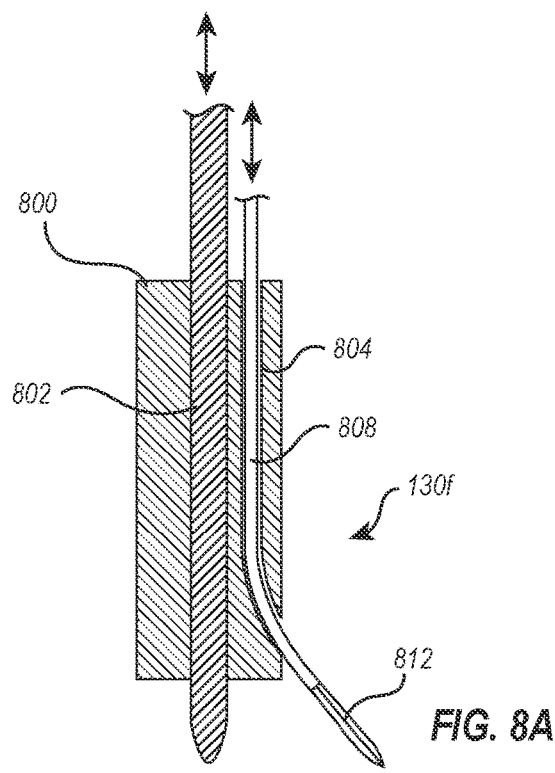
FIGS. 8A-8C illustrate yet another embodiment of a cutting mechanism according to the present disclosure shown in use in association with a cardiac valve.
Figure 8B:
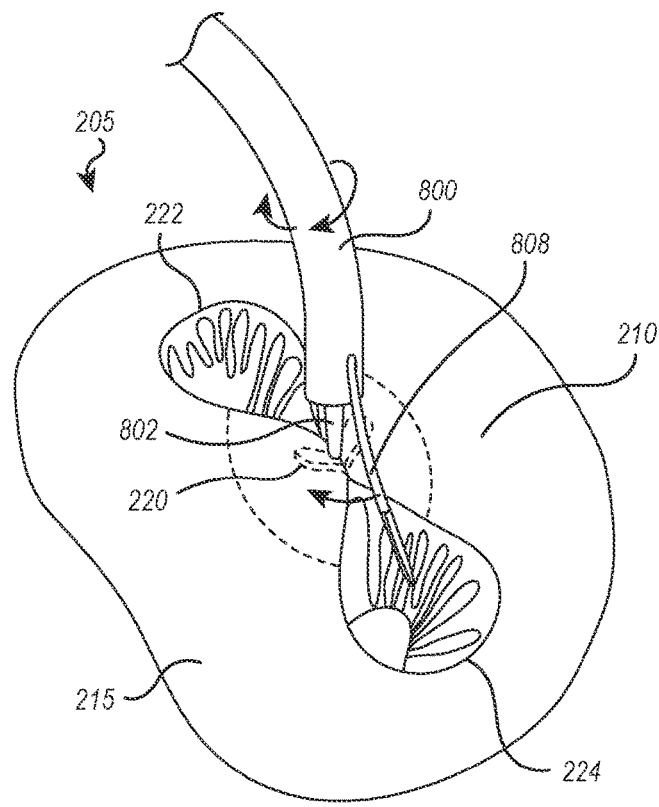
Figure 8C:
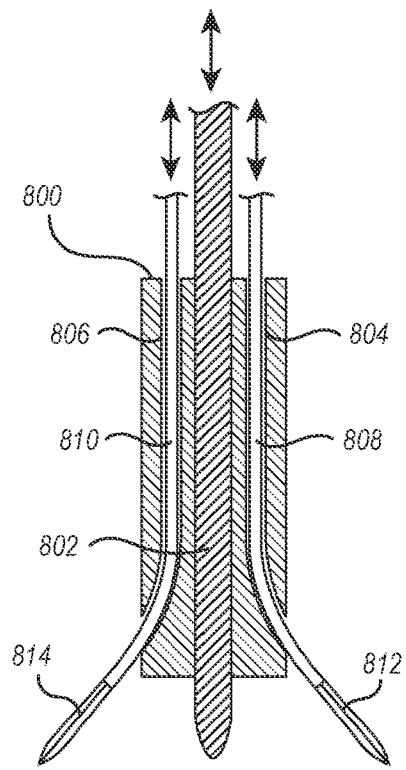

Finally, reference is next made to FIGS. 8A-8C, which illustrate still yet another embodiment of a cutting mechanism for use in detaching an interventional device from one or more leaflets of a mitral valve. In this embodiment, cutting mechanism 130*f* can include an inner catheter or hypotube 800 and a flexible stabilizing rod or dilator 802. As shown, stabilizing rod 802 extends through the inner lumen of hypotube 800 and can be selectively advanced and/or retracted relative to hypotube 800. The guide catheter is not shown in FIGS. 8A and 8C, but it should be understood that cutting mechanism 130f is intended for use within a suitable guide catheter to position the distal end of cutting mechanism 130f above the interventional device 220. Once properly positioned, stabilizing rod 802 can be advanced relative to the guide catheter and hypotube 800 so as to extend beyond the distal end of hypotube 800 by a predetermined distance. With the stabilizing rod 802 advanced, the entire system can be advanced distally, until the distal end of stabilizing rod 802 engages the fold of leaflet tissue located opposite the interventional clip 220, which fold is created when the posterior and anterior leaflets 210 and 215 are brought and held together by interventional device 220.

As shown in FIGS. 8A and 8C, hypotube 800 can include one or more lumens formed in the wall of hypotube 800, such as lumen 804 shown in FIG. 8A and lumens 804 and 806 shown in FIG. 8B. As illustrated, each lumen 804 and 806, extends from the proximal end of hypotube 800 and then exits at an angle laterally outwardly from the side wall of hypotube 800 near the distal end of hypotube 800. Positioned within each lumen 804 and 806 is an elongated cutter 808 and 810. Each cutter 808 and 810 preferably terminates in a cutting blade portion 812 and 184 at its distal end, and can be selectively advanced and retracted relative to hypotube 800. As shown in FIGS. 8A and 8C, when cutters 808 and 810 are advanced to extend beyond hypotube 800, the distal ends of cutter 808 and 810 splay radially outwardly at an angle relative to the central axis of hypotube 800.

In the case of the embodiment shown in FIG. 8A, once the distal end of the stabilizing rod 802 is firmly engaged against the leaflet fold opposite the interventional device 220 as described above, then cutter 808 can be advanced to extend out and beyond the end of hypotube 800. In some instances, the advancement of cutter 808 will also extend through one of the orifices 210 or 215, but it may also be necessary to further advance hypotube 800 relative to stabilizing rod 802 until cutter 808 extends into orifice 222 or 224. At that point, hypotube 800 alone or hypotube 800 and the guide catheter 105 together can be rotated around stabilizing rod 802, thereby causing the cutting blade 812 of cutter 808 to slice through the leaflet tissue in an arcuate path around interventional device 220 as schematically illustrated in FIG. 8B. With a single cutter 808, a rotation of 180 degrees should be sufficient to detach one leaflet from the interventional device 220, and a rotation of 360 degrees should be sufficient to detach both leaflets from the interventional device. As will be appreciated, the embodiment shown in FIG. 8C operates in a substantially similar manner, except that each cutter 808 and 810 can simultaneously be inserted through both orifices, and cutting of both leaflets can be completed with a single rotation of 180 degrees.

In describing the various embodiments above, the description may at times have explicitly discussed one particular mitral valve leaflet, such as anterior leaflet 215. It should be understood and appreciated, however, that the invention is not intended to be limited to either specific leaflet, but instead can be used to cut either anterior leaflet 215, posterior leaflet 210, or both.

It should also be understood that the order of manipulation of components of the various embodiments as described above are provided as representative examples only, and changes in the order of manipulation that may be readily understood by those skilled in the art are intended to be encompassed within the scope of this disclosure.

Further still, in addition to the embodiments described above, it should also be understood that individual components from one embodiment could also be combined with and/or substituted for a comparable component described in a different embodiment. For example, the stabilizing rod 802 disclosed in relation to the embodiment shown in FIGS. 8A-8C could also be incorporated into one or more of the other embodiments, such as, for example, the embodiment illustrated in FIGS. 3A-3D. Similarly, the cutting blades and structure shown in FIGS. 8A and 8C could be substituted in place of the cutting blade shown in FIGS. 7A-7C, or vice versa.

Similarly, while many of the embodiments discussed above contemplate mechanical cutting of leaflet tissue by means of sharpened edges of a cutting element, it should be further understood that such embodiments could also be adapted to include suitable electrical connections between the cutting element and a source of electrosurgical energy so that such cutting elements may accomplish cutting of tissue by mechanical cutting, by the application of electrosurgical energy to surrounding tissue through the cutting element, or by a combination of both.

Also, with any or all of the foregoing embodiments, one or more components of the leaflet cutting system can also include one or more radiopaque and/or echogenic markers to aid in the visualization of such components during a procedure. For example, one or more radiopaque and/or echogenic markers can be provided on the distal end 115 and/or the steerable portion 117 of the guide catheter 105. Similarly, one or more radiopaque and/or echogenic markers can also be provided on various components of the different embodiments of the cutting mechanisms described above, including, but not limited to such markings being provided on the distal ends of the inner catheter, hypotube, clip grasping structures, cutting blades, stabilizing rods, etc.

One skilled in the art will appreciate that the present invention is not limited to use within the mitral valve. The cardiac valve could also be the tricuspid aortic, pulmonic valve, etc. More generally, the embodiments described herein may be applied in other implementations involving removal of a previously implanted or deployed device from tissue. Further, although figures show the guide catheter 105 extending through the interatrial septum 200, the present invention is not limited to use via a transseptal approach. Any suitable delivery approach may be used, including transfemoral, radial, transjugular, or transapical.

Following are some further example embodiments of the invention. These are presented only by way of example and are not intended to limit the scope of the invention in any way.

Embodiment 1. A system for cutting leaflet tissue at a cardiac valve, comprising a guide catheter having a proximal end and a distal end, wherein the distal end of the guide catheter is steerable to a position above a cardiac valve, a handle coupled to the proximal end of the guide catheter, the handle comprising at least one control configured to steer the guide catheter to the position above the cardiac valve, and a cutting mechanism routable through the guide catheter and able to be positioned at the distal end of the guide catheter, the cutting mechanism configured to cut a portion of leaflet tissue of the cardiac valve.

Embodiment 2. The system of embodiment 1, wherein the at least one control is further configured to provide selective actuation of the cutting mechanism.

Embodiment 3. The system in any of embodiments 1 to 2, wherein the guide catheter is introduced transseptally.

Embodiment 4. The system in any of embodiments 1 to 3, further comprising an indeflator attached to the guide catheter, the indeflator configured to hold the leaflet in place by applying negative pressure.

Embodiment 5. The system in any of embodiments 1 to 4, wherein the guide catheter is U-shaped.

Embodiment 6. The system in any of embodiments 1 to 5, wherein: the cutting mechanism comprises two blades joined at a pivot point, wherein the two blades each comprise a cutting edge disposed on an outside surface of each of the two blades and the two blades are oriented and shaped such that they cut the portion of leaflet tissue of the cardiac valve in a predefined arc; and the cutting mechanism is configured to extend from the distal end of the guide catheter.

Embodiment 7. The system in any of embodiments 1 to 6, wherein: the cutting mechanism comprises a hypotube with a sharped end that terminates in a point, wherein the sharpened end is configured to cut the portion of leaflet tissue of the cardiac valve in a predefined arc; and the cutting mechanism is configured to extend from the distal end of the guide catheter.

Embodiment 8. The system in any of embodiments 1 to 7, wherein: the cutting mechanism comprises a first and a second delivery catheter, each comprising a proximal end and a distal end; each of the first and second delivery catheters comprises a rotatable paddle joined to the delivery catheter by a joint at the distal end of the delivery catheter; each of the first and second delivery catheters comprises a gripping mechanism rotatable around the joint and positioned between the first delivery catheter and the rotatable paddle of the first delivery catheter, and the second delivery catheter and the rotatable paddle of the second delivery catheter; and a wire extending from the joint of the first delivery catheter to the joint of the second delivery catheter.

Embodiment 9. The system in any embodiments 1 to 8, wherein: the first delivery catheter is configured to extend from the distal end of the guide catheter thereby extending the rotatable paddle of the first delivery catheter into a first orifice of the cardiac valve, the gripping mechanism of the first delivery catheter and the rotatable paddle of the first delivery catheter are configured to secure leaflet tissue therebetween, the second delivery catheter is configured to extend from the distal end of the guide catheter thereby extending the rotatable paddle of the second delivery catheter into a second orifice of the cardiac valve, and the gripping mechanism of the second delivery catheter and the rotatable paddle of the second delivery catheter are configured to secure leaflet tissue therebetween.

Embodiment 10. The system in any of embodiments 1 to 9, wherein the gripping mechanism of each of the first and second guide catheters secures the leaflet tissue on an atrial side, and the rotatable paddle of each of the first and second guide catheters secures the leaflet tissue on a ventricular side.

Embodiment 11. The system in any of embodiments 1 to 10, wherein: the wire is configured to rotate around a hub within the joint of each of the first and second delivery catheters; and the wire configured to selectively provide radio frequency current energy to the portion of leaflet tissue of the cardiac valve, thereby cutting the portion of leaflet tissue when rotated around the hub within the joint of each of the first and second delivery catheters.

Embodiment 12. The system in any of embodiments 1 to 11, further comprising a clip grasping structure comprising an elongated portion and a distal clamping portion; wherein: the distal clamping portion of the clip grasping structure is extendable distally past the distal end of the guide catheter and configured to secure an interventional implant that approximates adjacent leaflets of the cardiac valve; and the distal clamping portion of the clip grasping structure is retractable proximally into the distal end of the guide catheter with the secured interventional implant.

Embodiment 13. The system in any of embodiments 1 to 12, wherein the distal clamping portion of the clip grasping structure comprises two prongs.

Embodiment 14. The system in any of embodiments 1 to 13, wherein: the cutting mechanism comprises a cutting wire comprising an elongated portion that terminates in a distal loop portion, the cutting wire extends from the handle to the distal end of the guide catheter, and the distal clamping portion of the clip grasping structure extends through the distal loop portion of the cutting wire when extending distally past the distal end of the guide catheter and retracting proximally into the distal end of the guide catheter with the secured interventional implant.

Embodiment 15. The system in any of embodiments 1 to 14, wherein: the cutting wire is configured to selectively provide radio frequency current energy, and the distal loop portion of the cutting wire is configured to cut the portion of leaflet tissue when the distal clamping portion of the clip grasping structure retracts proximally into the distal end of the guide catheter with the secured interventional implant.

Embodiment 16. The system in any of embodiments 1 to 15, wherein the cutting wire is configured to detach the interventional implant from the surrounding leaflet tissue.

Embodiment 17. The system in any of embodiments 1 to 16, further comprising a hypotube routable through the guide catheter and able to be positioned at the distal end of the guide catheter, wherein the clip grasping structure is further routable through the hypotube and able to be positioned at a distal end of the hypotube.

Embodiment 18. The system in any of embodiments 1 to 17, wherein the hypotube is configured to extend from the distal end of the guide catheter when the distal clamping portion of the clip grasping structure is extended distally past the distal end of the guide catheter such that the hypotube encloses a proximal portion of the distal clamping portion of the clip grasping structure within the hypotube, thereby causing the distal clamping portion of the clip grasping structure to secure an interventional implant.

Embodiment 19. The system in any of embodiments 1 to 18, wherein the cutting mechanism comprises an elongated cutter configured to extend from the distal end of the guide catheter and rotate around a horizontal arc, thereby cutting the portion of leaflet tissue.

Embodiment 20. The system in any of embodiments 1 to 19, wherein the elongated cutter is configured to selectively provide radio frequency current energy to the portion of leaflet tissue of the cardiac valve, thereby cutting the portion of leaflet tissue when rotated around the horizontal arc.

Embodiment 21. A method of cutting leaflet tissue at a cardiac valve within a body, comprising positioning a guide catheter, having a proximal and a distal end such that the distal end of the guide catheter is positioned at a cardiac valve, routing a cutting mechanism through the guide catheter such that the cutting mechanism extends to the distal end of the guide catheter, wherein the cardiac valve is associated with an interventional implant that approximates adjacent leaflets of the cardiac valve, and a cutting mechanism extends from the guide catheter; and actuating the cutting mechanism to cut at a portion of least one leaflet of the approximated adjacent leaflet.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes that come within the meaning and range of equivalency of the claims are to be embraced within their scope.

We claim:

1. A system for severing leaflet tissue at a cardiac valve, comprising:
   a guide catheter having a proximal end and a distal end, wherein the distal end of the guide catheter is steerable to a position above a cardiac valve;
   a handle coupled to the proximal end of the guide catheter, the handle comprising at least one control configured to steer the guide catheter to the position above the cardiac valve;
   a cutting mechanism routable through the guide catheter and able to be positioned at the distal end of the guide catheter, the cutting mechanism configured to sever a portion of leaflet tissue of the cardiac valve, wherein the cutting mechanism comprises:
   a hypotube having a proximal end and a distal end with a lumen extending therebetween;
   a tapering blade portion extending distally from a portion of the circumference of the distal end of the hypotube, the blade portion terminating at a distal most point longitudinally aligned with a first edge along the circumference of the hypotube;
   wherein arcuate sharpened outer edges extend from the distal most point, the sharpened edges tapering proximally and radially outward along a circumference of the hypotube, the sharpened edges terminating at a second edge diametrically opposed from the first edge; and
   wherein the cutting mechanism is configured to sever the portion of leaflet tissue of the cardiac valve in a predefined arc around an interventional implant.

2. The system of claim 1, wherein the at least one control is further configured to provide selective actuation of the cutting mechanism.

3. The system of claim 1, wherein the guide catheter is introduced transseptally.

4. The system of claim 1, further comprising an indeflator attached to the guide catheter, the indeflator configured to hold the leaflet in place by applying negative pressure.

5. The system of claim 1, wherein the guide catheter is U-shaped.

6. The system of claim 1, wherein:
   the cutting mechanism comprises two blades joined at a pivot point, wherein the two blades each comprise a cutting edge disposed on an outside surface of each of the two blades and the two blades are oriented and shaped such that they sever the portion of leaflet tissue of the cardiac valve in a predefined arc; and
   the cutting mechanism is configured to extend from the distal end of the guide catheter.

7. The system of claim 1, wherein the cutting mechanism is configured to extend from the distal end of the guide.

8. The system of claim 1, wherein:
   the cutting mechanism comprises a first and a second delivery catheter, each comprising a proximal end and a distal end;
   each of the first and second delivery catheters comprises a rotatable paddle joined to the delivery catheter by a joint at the distal end of the delivery catheter;
   each of the first and second delivery catheters comprises a gripping mechanism rotatable around the joint and positioned between the first delivery catheter and the rotatable paddle of the first delivery catheter, and the second delivery catheter and the rotatable paddle of the second delivery catheter; and
   a wire extending from the joint of the first delivery catheter to the joint of the second delivery catheter.

9. The system of claim 8, wherein:
   the first delivery catheter is configured to extend from the distal end of the guide catheter thereby extending the rotatable paddle of the first delivery catheter into a first orifice of the cardiac valve;
   the gripping mechanism of the first delivery catheter and the rotatable paddle of the first delivery catheter are configured to secure leaflet tissue therebetween;
   the second delivery catheter is configured to extend from the distal end of the guide catheter thereby extending the rotatable paddle of the second delivery catheter into a second orifice of the cardiac valve; and
   the gripping mechanism of the second delivery catheter and the rotatable paddle of the second delivery catheter are configured to secure leaflet tissue therebetween.

10. The system of claim 9, wherein the gripping mechanism of each of the first and second guide catheters secures the leaflet tissue on an atrial side, and the rotatable paddle of each of the first and second guide catheters secures the leaflet tissue on a ventricular side.

11. The system of claim 9, wherein:
    the wire is configured to rotate around a hub within the joint of each of the first and second delivery catheters; and
    the wire configured to selectively provide radio frequency current energy to the portion of leaflet tissue of the cardiac valve, thereby cutting the portion of leaflet tissue when rotated around the hub within the joint of each of the first and second delivery catheters.

12. The system of claim 1, further comprising a clip grasping structure comprising an elongated portion and a distal clamping portion; wherein:
    the distal clamping portion of the clip grasping structure is extendable distally past the distal end of the guide catheter and configured to secure an interventional implant that approximates adjacent leaflets of the cardiac valve; and
    the distal clamping portion of the clip grasping structure is retractable proximally into the distal end of the guide catheter with the secured interventional implant.

13. The system of claim 12, wherein the distal clamping portion of the clip grasping structure comprises two prongs.

14. The system of claim 12, wherein:
    the cutting mechanism comprises a cutting wire comprising an elongated portion that terminates in a distal loop portion;
    the cutting wire extends from the handle to the distal end of the guide catheter; and
    the distal clamping portion of the clip grasping structure extends through the distal loop portion of the cutting wire when extending distally past the distal end of the guide catheter and retracting proximally into the distal end of the guide catheter with the secured interventional implant.

15. The system of claim 14, wherein:
    the cutting wire is configured to selectively provide radio frequency current energy; and
    the distal loop portion of the cutting wire is configured to sever the portion of leaflet tissue when the distal clamping portion of the clip grasping structure retracts proximally into the distal end of the guide catheter with the secured interventional implant.

16. The system of claim 14, wherein the cutting wire is configured to detach the interventional implant from surrounding leaflet tissue.

17. The system of claim 12, further comprising a hypotube routable through the guide catheter and able to be positioned at the distal end of the guide catheter, wherein the clip grasping structure is further routable through the hypotube and able to be positioned at a distal end of the hypotube.

18. The system of claim 17, wherein the hypotube is configured to extend from the distal end of the guide catheter when the distal clamping portion of the clip grasping structure is extended distally past the distal end of the guide catheter such that the hypotube encloses a proximal portion of the distal clamping portion of the clip grasping structure within the hypotube, thereby causing the distal clamping portion of the clip grasping structure to secure an interventional implant.

19. The system of claim 17, wherein the cutting mechanism comprises an elongated cutter configured to extend from the distal end of the guide catheter and rotate around a horizontal arc, thereby cutting the portion of leaflet tissue.

20. The system of claim 19, wherein the elongated cutter is configured to selectively provide radio frequency current energy to the portion of leaflet tissue of the cardiac valve, thereby cutting the portion of leaflet tissue when rotated the horizontal arc.

21. A method of cutting leaflet tissue at a cardiac valve within a body, comprising:

positioning a guide catheter, having a proximal and a distal end such that the distal end of the guide catheter is positioned at a cardiac valve;

routing a cutting mechanism through the guide catheter such that the cutting mechanism extends to the distal end of the guide catheter, wherein the cardiac valve is associated with an interventional implant that approximates adjacent leaflets of the cardiac valve, and a cutting mechanism extends from the guide catheter, and the cutting mechanism comprises:

a hypotube having a proximal end and a distal end with a lumen extending therebetween;

a tapering blade portion extending distally from a portion of the circumference of the distal end of the hypotube, the blade portion terminating at a distal most point longitudinally aligned with a first edge along the circumference of the distal end of the hypotube;

wherein arcuate sharpened outer edges extend from the distal most point, the sharpened outer edges tapering proximally and radially outward along a circumference of the hypotube, terminating at a second edge diametrically opposed from the first edge, wherein the cutting mechanism is configured to sever the portion of leaflet tissue of the cardiac valve in a predefined arc; and actuating the cutting mechanism to sever at a portion of at least one leaflet of the approximated adjacent leaflet.

* * * * *